US012669580B2

(12) United States Patent
Rimini et al.

(10) Patent No.: US 12,669,580 B2
(45) Date of Patent: Jun. 30, 2026

(54) WIRELESS COMMUNICATION WITH ENHANCED MAXIMUM PERMISSIBLE EXPOSURE (MPE) COMPLIANCE

(71) Applicant: QUALCOMM Incorporated, San Diego, CA (US)

(72) Inventors: Roberto Rimini, San Diego, CA (US); Tsai-Chen Huang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 124 days.

(21) Appl. No.: 17/734,985

(22) Filed: May 2, 2022

(65) Prior Publication Data

US 2022/0260676 A1 Aug. 18, 2022

Related U.S. Application Data

(63) Continuation of application No. 16/548,722, filed on Aug. 22, 2019, now Pat. No. 11,320,517.

(51) Int. Cl.
*G01S 7/41* (2006.01)
*G01S 7/40* (2006.01)
(Continued)

(52) U.S. Cl.
CPC ............. *G01S 7/411* (2013.01); *G01S 7/4013* (2021.05); *H04B 7/043* (2013.01); *H04W 52/28* (2013.01);
(Continued)

(58) Field of Classification Search
CPC .... G01S 13/931; G01S 7/4008; G01S 13/726; G01S 13/536; G01S 7/411; G01S 17/42;
(Continued)

(56) References Cited

U.S. PATENT DOCUMENTS

| 5,731,778 A | 3/1998 | Nakatani et al. |
| 6,147,638 A | 11/2000 | Rohling et al. |
| | (Continued) | |

FOREIGN PATENT DOCUMENTS

| CN | 102088903 A | 6/2011 |
| CN | 102565780 A | 7/2012 |
| | (Continued) | |

OTHER PUBLICATIONS

Akdeniz et al., "Millimeter Wave Channel Modeling and Cellular Capacity Evaluation", IEEE JSAC, vol. 32, No. 6, Jun. 2014, pp. 1164-1179 Akdeniz_0614.pdf.
(Continued)

*Primary Examiner* — Tuan A Vu

(74) *Attorney, Agent, or Firm* — Paul M. McAdams; Shumaker & Sieffert, P.A.

(57) ABSTRACT

Aspects of the disclosure relate to classifying a target object. An electronic device may transmit a detection signal and receive a reflection signal reflected from the target object. The electronic device then determines, based on one or more features of the reflection signal, a category of the target object and adjusts at least one transmission parameter based on the category. The electronic device then transmits an adjusted signal using the transmission parameter. Other aspects, embodiments, and features are also claimed and described.

30 Claims, 8 Drawing Sheets

(51) Int. Cl.

| | |
|---|---|
| *H04B 7/0426* | (2017.01) |
| *H04W 52/28* | (2009.01) |
| *H04W 52/36* | (2009.01) |
| *A61B 3/10* | (2006.01) |
| *A61B 5/00* | (2006.01) |
| *G01J 3/433* | (2006.01) |
| *G01S 13/28* | (2006.01) |

(52) U.S. Cl.
CPC .......... *H04W 52/367* (2013.01); *A61B 3/102* (2013.01); *A61B 5/4815* (2013.01); *G01J 3/4338* (2013.01); *G01S 13/28* (2013.01)

(58) Field of Classification Search
CPC ............ G01S 7/4013; H04W 52/0245; H04W 52/367; H04W 52/28; H04W 72/542; H04B 1/38; H04B 7/22; H04B 7/043; H01Q 3/40; A61B 5/05; H04L 7/042; G10L 17/26
See application file for complete search history.

(56) References Cited

U.S. PATENT DOCUMENTS

| | | | | |
|---|---|---|---|---|
| 8,398,558 | B2 | 3/2013 | Thijs et al. | |
| 9,110,152 | B2 | 8/2015 | Ando et al. | |
| 9,515,378 | B2 | 12/2016 | Prasad | |
| 9,766,324 | B2 | 9/2017 | Katz et al. | |
| 9,915,726 | B2 | 3/2018 | Bailey et al. | |
| 10,812,125 | B1 * | 10/2020 | Badic ................. | H04W 72/542 |
| 11,169,251 | B2 | 11/2021 | Sahin et al. | |
| 2003/0064761 | A1 * | 4/2003 | Nevermann ........ | H04W 52/367 455/572 |
| 2005/0156110 | A1 | 7/2005 | Crawely | |
| 2006/0208169 | A1 | 9/2006 | Breed et al. | |
| 2008/0272956 | A1 | 11/2008 | Pedersen et al. | |
| 2011/0144573 | A1 | 6/2011 | Rofougaran et al. | |
| 2012/0113431 | A1 | 5/2012 | Fukuma et al. | |
| 2013/0106657 | A1 | 5/2013 | Perthold et al. | |
| 2013/0157729 | A1 * | 6/2013 | Tabe ................. | H04W 52/0245 977/932 |
| 2014/0118186 | A1 | 5/2014 | Nakanishi et al. | |
| 2014/0340569 | A1 | 11/2014 | Raskar et al. | |
| 2015/0127343 | A1 * | 5/2015 | Mullor .................... | G10L 17/26 704/244 |
| 2015/0133173 | A1 | 5/2015 | Edge et al. | |
| 2015/0182162 | A1 | 7/2015 | Zhao | |
| 2015/0378008 | A1 * | 12/2015 | Ookawa ................ | G01S 13/931 342/194 |
| 2016/0006914 | A1 | 1/2016 | Neumann | |
| 2016/0327634 | A1 * | 11/2016 | Katz .................... | G01S 7/4008 |
| 2016/0351996 | A1 | 12/2016 | Ou | |
| 2017/0042432 | A1 * | 2/2017 | Adib .................... | G01S 13/536 |
| 2017/0059688 | A1 | 3/2017 | Gan | |
| 2017/0082741 | A1 * | 3/2017 | Adib .................... | G01S 13/726 |
| 2017/0102457 | A1 | 4/2017 | Li et al. | |
| 2017/0127398 | A1 | 5/2017 | Andgart et al. | |
| 2017/0172425 | A1 * | 6/2017 | Liu .......................... | A61B 5/05 |
| 2017/0311901 | A1 | 11/2017 | Zhao et al. | |
| 2018/0059248 | A1 * | 3/2018 | O'Keeffe ................ | G01S 17/42 |
| 2018/0103485 | A1 | 4/2018 | Jiang et al. | |
| 2018/0287651 | A1 | 10/2018 | Fernando et al. | |
| 2018/0372874 | A1 | 12/2018 | Lipson et al. | |
| 2019/0007256 | A1 * | 1/2019 | Chen ........................ | H04B 1/38 |
| 2019/0011549 | A1 | 1/2019 | Mercuri et al. | |
| 2019/0123442 | A1 * | 4/2019 | Vannucci ................. | H01Q 3/40 |
| 2019/0166030 | A1 * | 5/2019 | Chen ........................ | H04L 7/042 |
| 2019/0175074 | A1 * | 6/2019 | Zhang ...................... | H04B 7/22 |
| 2019/0178985 | A1 | 6/2019 | Roh | |
| 2020/0028262 | A1 | 1/2020 | Fang | |
| 2020/0081093 | A1 | 3/2020 | Rimini et al. | |
| 2020/0134344 | A1 | 4/2020 | Joshi et al. | |
| 2021/0055385 | A1 | 2/2021 | Rimini et al. | |
| 2021/0055386 | A1 | 2/2021 | Rimini | |

FOREIGN PATENT DOCUMENTS

| | | | |
|---|---|---|---|
| CN | 106659428 | A | 5/2017 |
| CN | 107636893 | A | 1/2018 |
| CN | 108153410 | A | 6/2018 |
| CN | 109171688 | A | 1/2019 |
| CN | 109924960 | A | 6/2019 |
| CN | 110058220 | A | 7/2019 |
| EP | 2303121 | A1 | 4/2011 |
| EP | 3154153 | A1 | 4/2017 |
| TW | 201836287 | A | 10/2018 |
| TW | 201838352 | A | 10/2018 |

OTHER PUBLICATIONS

Anitori L., et al., "FMCW Radar for Life-sign Detection," IEEE National Radar Conference, May 4-8, 2009, Proceedings., pp. 1-6, 10.1109/RADAR.2009.4976934.

International Search Report and Written Opinion—PCT/US2019/048723—ISA/EPO—Apr. 7, 2020.

International Search Report and Written Opinion—PCT/US2020/047550—ISA/EPO—Nov. 18, 2020.

Partial International Search Report—PCT/US2020/047550—ISA/EPO—Sep. 25, 2020.

Rangan S., et al., "Millimeter-Wave Cellular Wireless Networks: Potentials and Challenges", Proceedings of the IEEE, Mar. 2014, vol. 102, Issue 3, pp. 366-385.

Taiwan Search Report—TW108131289—TIPO—Feb. 24, 2023.

* cited by examiner

FIG. 4

502 ⟍
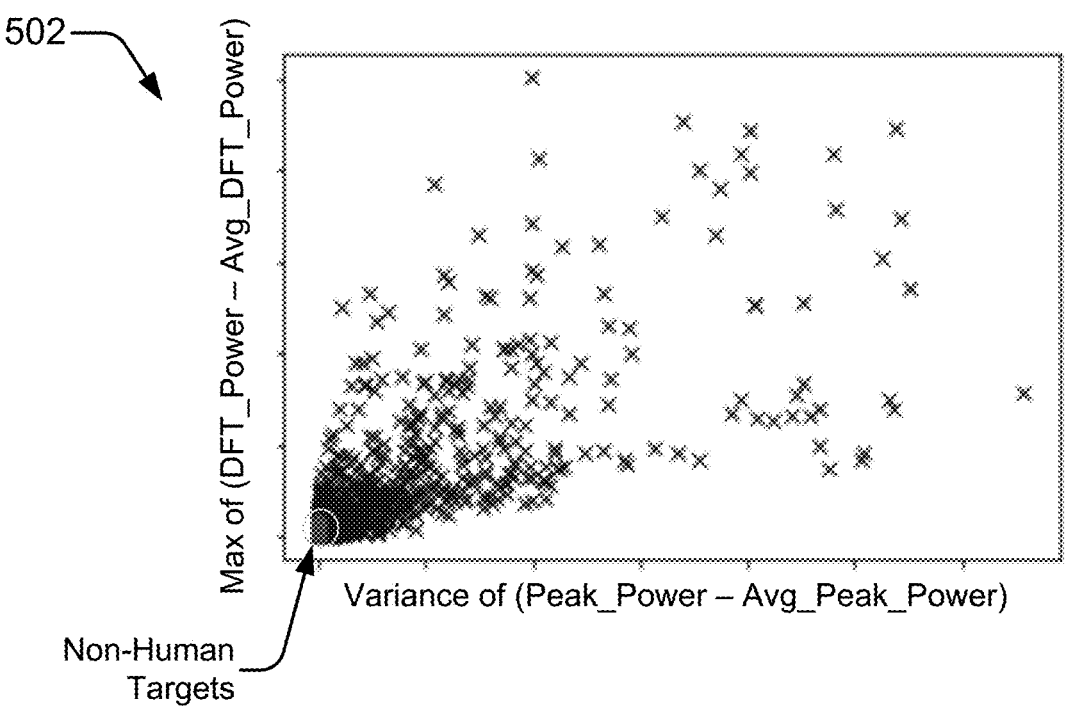
504 ⟍
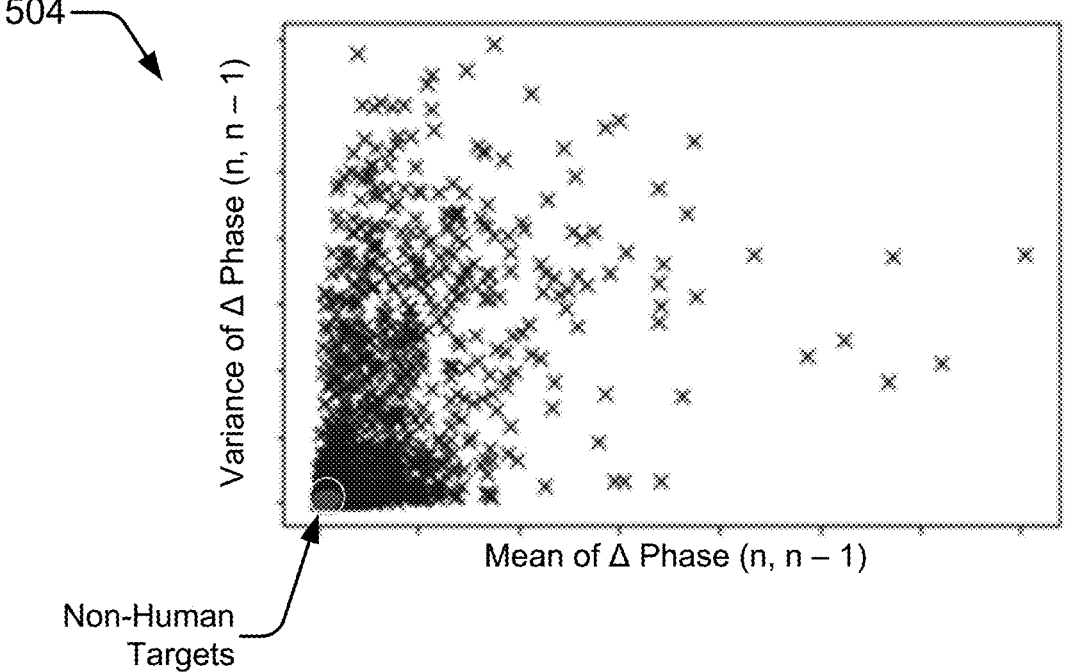
FIG. 5

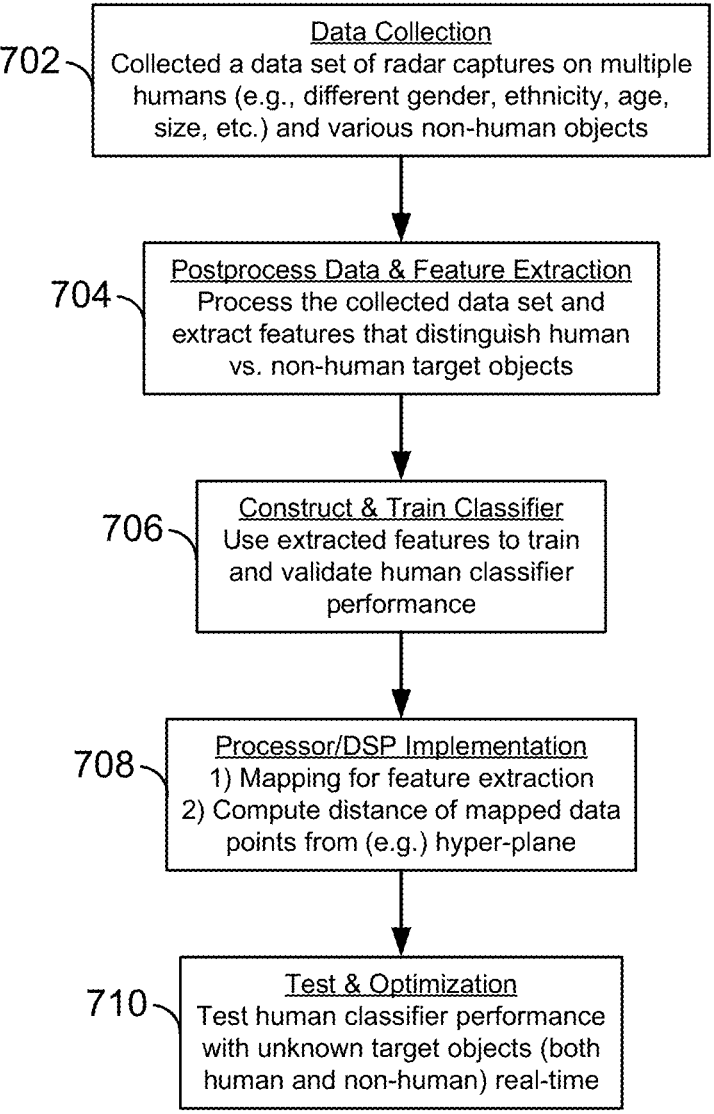

702 — Data Collection
Collected a data set of radar captures on multiple humans (e.g., different gender, ethnicity, age, size, etc.) and various non-human objects 704 — Postprocess Data & Feature Extraction
Process the collected data set and extract features that distinguish human vs. non-human target objects 706 — Construct & Train Classifier
Use extracted features to train and validate human classifier performance 708 — Processor/DSP Implementation
1) Mapping for feature extraction
2) Compute distance of mapped data points from (e.g.) hyper-plane 710 — Test & Optimization
Test human classifier performance with unknown target objects (both human and non-human) real-time

FIG. 7

WIRELESS COMMUNICATION WITH ENHANCED MAXIMUM PERMISSIBLE EXPOSURE (MPE) COMPLIANCE

CROSS-REFERENCE TO RELATED APPLICATION

This application for patent is a continuation of co-pending U.S. patent application Ser. No. 16/548,722, filed on Aug. 22, 2019, assigned to the assignee hereof and hereby incorporated herein by reference in its entirety as if fully set forth below and for all applicable purposes.

TECHNICAL FIELD

The technology discussed below relates generally to wireless communication and/or object classification systems, and more particularly, to machine-learning-based wireless emissions control as well as object classification for controlling maximum permissible exposure. Embodiments can provide and enable techniques for classifying nearby subjects and/or target objects (e.g., those detected by a wireless proximity sensor or other communication-enabling components) and controlling for maximum permissible exposure.

INTRODUCTION

Next-generation wireless telecommunication systems (e.g., such as Fifth Generation (5G) or New Radio (NR) technologies) are being deployed utilizing millimeter-wave (mmW) signals. These signals can operate, for example, at a 28 GHz and 39 GHz spectrum. Although higher frequency signals provide larger bandwidths to efficiently communicate vast amounts of information/data, mmW signals may suffer from high path loss (e.g., path attenuation). To compensate for path loss, transmit power levels can be increased, or beamforming can concentrate energy in a particular direction.

As with various types of electronic signal transmissions, there are usually regulatory rules governing transmission strengths. For example, for mmW signals, the US Federal Communications Commission (FCC) and other regulatory bodies set stringent RF exposure requirements. These rules ensure that the maximum permissible exposure (MPE) on human skin does not exceed a power density of 1 mW/cm$^2$. To meet targeted guidelines, electronic devices are responsible for balancing performance with transmission power and other constraints. This balancing act can be challenging to achieve, especially with devices that have cost, size, and other concerns.

BRIEF SUMMARY OF SOME EXAMPLES

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

According to some aspects, wireless communication devices, methods, and systems are provided to enable MPE compliance and/or human target object awareness and detection. For example, a device embodiment (e.g. a mobile apparatus) may include a wireless communication enabling component (e.g., an mmW signal interface). A wireless communication enabling component (e.g., a transceiver) can not only facilitate wireless communication via receipt and transfer of radio frequency signals (e.g., mmW signals), a transceiver can also leverage mmW signaling to detect objects. A device embodiment can utilize object detection features to determine classes of objects. If objects are determined to be human, non-human, animate, inanimate, etc., the device can adjust operating parameters of a communication interface (e.g., a mmW transceiver) for MPE compliance (e.g., power up or power down signal transmissions). According to some aspects, signal transmission power adjustments can occur in real time or according to a variety of desired timing arrangements.

In some aspects the disclosure provides a method for classification of a target object. The method includes transmitting a detection signal and receiving a reflection signal reflected from the target object. The method further includes determining, based on one or more features of the reflection signal, a category of the target object, and adjusting at least one transmission parameter based on the category of the target object. The method further includes transmitting an adjusted signal using the transmission parameter.

In further aspects, the disclosure provides an electronic device configured for classification of a target object. The electronic device includes a processor, a transceiver communicatively coupled to the processor, and a data storage medium communicatively coupled to the processor. Here, the processor is configured for transmitting a detection signal via the transceiver and receiving a reflection signal via the transceiver, the reflection signal reflected from the target object. The processor is further configured for determining, based on one or more features of the reflection signal, a category of the target object and adjusting at least one transmission parameter based on the category of the target object. The processor is further configured for transmitting, via the transceiver, an adjusted signal using the transmission parameter.

In further aspects, the disclosure provides an electronic device configured for classification of a target object. The electronic device includes means for transmitting a detection signal and means for receiving a reflection signal, the reflection signal reflected from the target object. The electronic device further includes means for determining, based on one or more features of the reflection signal, a category of the target object, and means for adjusting at least one transmission parameter based on the category of the target object. The electronic device further includes means for transmitting an adjusted signal using the transmission parameter.

In further aspects, the disclosure provides a non-transitory computer readable medium storing computer executable code. The code includes instructions for causing an electronic device to transmit a detection signal and instructions for causing the electronic device to receive a reflection signal reflected from the target object. The code further includes instructions for causing the electronic device to determine, based on one or more features of the reflection signal, a category of the target object, and instructions for causing the electronic device to adjust at least one transmission parameter based on the category of the target object. The code further includes instructions for causing the electronic device to transmit an adjusted signal using the transmission parameter.

In further aspects, the disclosure provides a wireless communication device including a housing shaped and sized to carry one or more components, including a memory, the wireless transceiver, a power amplifier, and at least one processor. The wireless transceiver is configured to transmit and/or receive millimeter wave signals via a wireless channel. The wireless transceiver is further configured to sense objects relative to and exterior the housing via millimeter wave signaling, and configured to provide object-sensing information to the at least one processor. And the at least one processor is configured to control the power amplifier to moderate a transmission parameter associated with the wireless transceiver transmitting and/or receiving millimeter waves based on the object-sensing information, and configured to convey information associated with sensing objects positioning relative to and exterior the housing.

In further aspects, the disclosure provides, in a system for providing information between a plurality of wireless communication devices, the information capable of assessing an object class of an observed object, a method of providing information to a wireless communication device. Here, the method includes configuring a data store to be in electrical wireless communication with one or more unique wireless communication devices among the plurality of wireless communication devices operating within a wireless network. The method further includes receiving micromovement information from the one or more unique wireless communication devices transmitted via a wireless network, the micromovement information including data observances indicating micromovements associated with one or more target objects. The method further includes determining object-class information for one or more target objects based at least in part on received micromovement information and other stored information. The method further includes transmitting the object-class information to one or more of the wireless communication devices in the wireless network such that any one of the wireless communication devices can moderate a wireless transmission parameter associated with its transmission and reception operations.

In further aspects, the disclosure provides a wireless communication device configured as a vehicle including a vehicle body configured to carry at least one of a payload or a passenger. The vehicle includes a wireless communication interface sized and shape to be placed in a location proximate or within the vehicle body, where the wireless communication interface is configured to transmit and/or receive millimeter wave signals via a wireless channel. The wireless communication interface is further configured to sense objects relative to the vehicle body via millimeter wave signaling and configured to provide object-sensing information to at least one processor. The at least one processor is configured to control a transmission parameter associated with the wireless communication interface transmitting and/or receiving millimeter waves based on the object-sensing information, and configured to convey information associated with sensing objects relative to the vehicle body.

In further aspects, the disclosure provides a wireless communication device configured for gaming, where the wireless communication device includes a housing sized and shaped for gaming to allow a user to participate in an electronic gaming environment. The wireless communication device includes a wireless communication interface sized and shaped to be placed in a location proximate or within the housing, where the wireless communication interface is configured to transmit and/or receive millimeter wave signals via a wireless channel. The wireless communication interface is further configured to sense objects relative to the housing via millimeter wave signaling, and configured to provide object-sensing information to at least one processor.

The at least one processor is configured to control a transmission parameter associated with the wireless communication interface transmitting and/or receiving millimeter waves based on the object-sensing information and configured to convey information associated with sensing objects relative to the housing.

In further aspects, the disclosure provides a method, apparatus, and software for causing a wireless communication device to transmit a plurality of detection signals and to receive, corresponding to the plurality of detection signals, a plurality of reflection signals reflected from a proximate object. The wireless communication device then transmits a transmission signal having a transmission parameter based on variations over time in one or more features of the plurality of reflection signals.

These and other aspects of the invention will become more fully understood upon a review of the detailed description, which follows. Other aspects, features, and embodiments will become apparent to those of ordinary skill in the art, upon reviewing the following description of specific, exemplary embodiments in conjunction with the accompanying figures. While features may be discussed relative to certain embodiments and figures below, all embodiments can include one or more of the advantageous features discussed herein. In other words, while one or more embodiments may be discussed as having certain advantageous features, one or more of such features may also be used in accordance with the various embodiments discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIG. 4 is a series of charts showing radar echo signatures of different target objects according to some aspects of the disclosure.

FIG. 5 is a series of charts showing two-dimensional feature spaces that illustrate how target object classification can be achieved based on the use of suitable features according to some aspects of the disclosure.

FIG. 7 is a flow chart illustrating an exemplary process for building a target object classifier according to some aspects of the disclosure.

DETAILED DESCRIPTION

Figure 1:
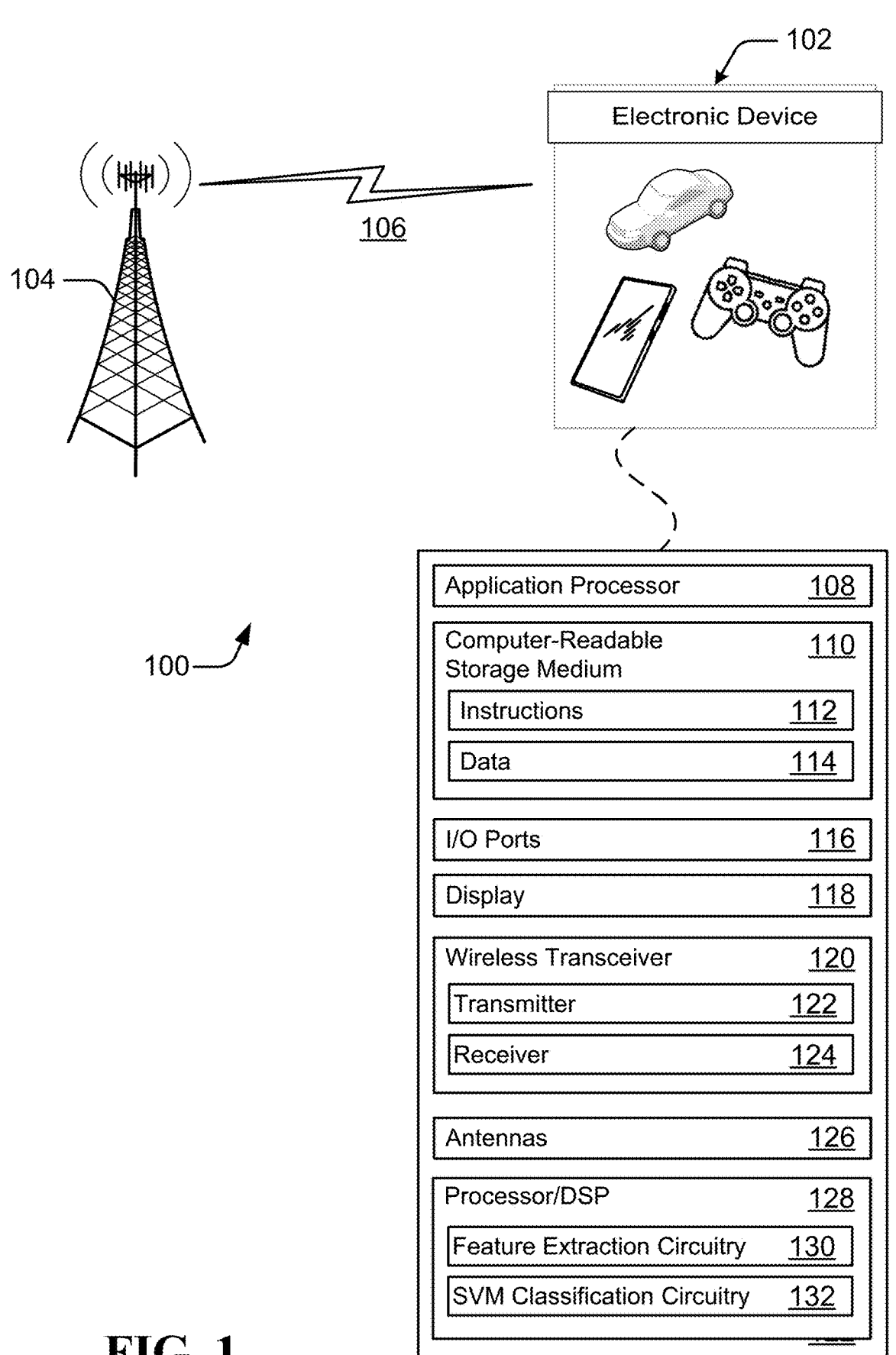
FIG. 1 is a block diagram of a wireless electronic device according to some aspects of the disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

While aspects and embodiments are described in this application by illustration to some examples, those skilled in the art will understand that additional implementations and use cases may come about in many different arrangements and scenarios. Innovations described herein may be implemented across many differing platform types, devices, systems, shapes, sizes, packaging arrangements. For example, embodiments and/or uses may come about via integrated chip embodiments and other non-module-component based devices (e.g., end-user devices, vehicles, communication devices, computing devices, industrial equipment, retail/ purchasing devices, medical devices, AI-enabled devices, etc.). While some examples may or may not be specifically directed to use cases or applications, a wide assortment of applicability of described innovations may occur. Implementations may range a spectrum from chip-level or modular components to non-modular, non-chip-level implementations and further to aggregate, distributed, or OEM devices or systems incorporating one or more aspects of the described innovations. In some practical settings, devices incorporating described aspects and features may also necessarily include additional components and features for implementation and practice of claimed and described embodiments. For example, transmission and reception of wireless signals necessarily includes a number of components for analog and digital purposes (e.g., hardware components including antenna, RF-chains, power amplifiers, modulators, buffer, processor(s), interleaver, adders/summers, etc.). It is intended that innovations described herein may be practiced in a wide variety of devices, chip-level components, systems, distributed arrangements, end-user devices, etc. of varying sizes, shapes and constitution.

An electronic wireless communication device that utilizes millimeter wave (mmW) signals may use a high transmit power to compensate for path loss associated with signals at these frequencies. Many of these electronic devices, such as a mobile user equipment (UE), can be physically operated by a user. Close physical proximity to such an electronic device presents opportunities for radiation to exceed a given guideline, such as a maximum permitted exposure (MPE) limit as determined by the Federal Communications Commission (FCC) or other regulatory body. Because of these issues, it is advantageous to enable devices to moderate one or more transmission parameters, including but not limited to transmit power, based on a proximity of the user.

Some proximity detection techniques may use a dedicated sensor, such as a camera, an infrared (IR) sensor, a radar sensor, etc. to detect a user However, these sensors may be bulky and expensive. Furthermore, a single electronic device can include multiple antennas that are positioned on different surfaces (e.g., on a top, a bottom, or opposite sides). To account for each of these antennas, according to some aspects, multiple cameras or sensors may need to be installed near each of these antennas, which further increases a cost and size of the electronic device.

In a further aspect and/or example, the same wireless transceiver utilized for wireless communication can also perform proximity detection. For example, local oscillator

6

(LO) circuitry within a wireless transceiver can generate one or more reference signals that can enable both proximity detection and wireless communication. The LO circuitry can enable a frequency-modulated continuous wave (FMCW) signal or a multi-tone signal to be transmitted for radar-based proximity detection. By analyzing reflections from either of these signals, a range (e.g., distance or slant range) to an object, and in some examples, a material composition of the object can be determined.

To ensure compliance with MPE requirements, according to some aspects, a proximity detector, including but not limited to an integrated FMCW-based radar function, can detect the presence of objects and/or nearby targets. Objects may be located around a device, and some objects may be targets of interest. For example, a detector can determine whether a target is within 20 cm of a device's radiating elements. Detection of multiple objects can be used to create a virtual map of items or subjects having spatial relationships to a device. Based on such proximity detection, a device can accordingly adjust one or more transmission parameters used for wireless communication, such as by reducing a transmission power, by switching to a different transmit antenna, etc. By actively measuring the range to one or more objects, an electronic device can continually monitor its surrounding environment, and can incrementally adjust one or more transmission parameters to account for the object's movement (e.g., adjustments can increase or decrease transmission power generally or in particular directions via beamformed mmWaves or RF waves).

In general, radar signal processing is tailored to extract a target's location-based information such as its distance, speed, angle, position, etc. However, a typical radar does not provide information about the nature of the target such as whether the target is a living animal/being, human, or not. According to an aspect of the present disclosure, it can be advantageous to adjust one or more transmission parameters used for wireless communication based not only on proximity detection of a nearby target, but in addition, based on a classification of the target. That is, MPE requirements generally only apply to exposure to human beings. If an inanimate object such as a coffee mug or a wall is in close proximity to an electronic device, then MPE requirements may not apply and a high transmission parameter (for example) can continue to be utilized. Therefore, including information about objects spaced away in spatial locations (e.g., a nearby target or subject located removed from the electronic device), or a classification of the detected proximate target, can help optimize the power transmission of the electronic device.

FIG. 1 illustrates an example electronic device 102 for implementing a machine learning (ML) algorithm to categorize target objects detected utilizing a radar-based proximity detector according to some aspects of this disclosure. In an example environment 100, the electronic device 102 communicates with a base station 104 through a wireless communication link 106 (wireless link 106). For example, the electronic device 102 and the base station 104 may be a part of a system for providing information between a plurality of unique wireless communication devices. In FIG. 1, the electronic device 102 is illustrated as a smart phone, a vehicle, or a gaming device, to provide some examples. However, an electronic device 102 may be any suitable stationary or mobile apparatus that includes a wireless transceiver. Within the present disclosure, the term electronic device broadly refers to a diverse array of devices and technologies. Electronic devices may include a number of hardware structural components sized, shaped, and arranged to help in communication; such components can include antennas, antenna arrays, RF chains, amplifiers, one or more processors, etc. electrically coupled to each other. For example, some non-limiting examples of a mobile apparatus include a mobile, a cellular (cell) phone, a smart phone, a session initiation protocol (SIP) phone, a laptop, a personal computer (PC), a notebook, a netbook, a smartbook, a tablet, a personal digital assistant (PDA), and a broad array of embedded systems, e.g., corresponding to an "Internet of things" (IoT). A mobile apparatus may additionally be an automotive or other transportation vehicle, a remote sensor or actuator, a robot or robotics device, a satellite radio, a global positioning system (GPS) device, an object tracking device, a drone, a multi-copter, a quad-copter, a remote control device, a consumer and/or wearable device, such as eyewear, a wearable camera, a virtual reality device, a smart watch, a health or fitness tracker, a digital audio player (e.g., MP3 player), a camera, a game console, a gaming device (e.g. an interface enabling a user to participate or play in an electronic game), etc. A mobile apparatus may additionally be a digital home or smart home device such as a home audio, video, and/or multimedia device, an appliance, a vending machine, intelligent lighting, a home security system, a smart meter, an augmented reality device, a virtual reality device, a mixed reality device, etc. A mobile apparatus may additionally be a smart energy device, a security device, a solar panel or solar array, a municipal infrastructure device controlling electric power (e.g., a smart grid), lighting, water, etc.; an industrial automation and enterprise device; a logistics controller; agricultural equipment; military defense equipment, vehicles, aircraft, ships, and weaponry, etc. Still further, a mobile apparatus may provide for connected medicine or telemedicine support, e.g., health care at a distance. Telehealth devices may include telehealth monitoring devices and telehealth administration devices, whose communication may be given preferential treatment or prioritized access over other types of information, e.g., in terms of prioritized access for transport of critical service data, and/or relevant QoS for transport of critical service data. In some examples, the electronic device 102 may be a wireless communication device including a housing shaped and sized to carry one or more components, such as those described below.

In one example, the electronic device 102 may be, or may be a part of, a vehicle that includes a vehicle body configured to carry at least one of a payload or a passenger. In this example, the wireless transceiver 120 may be sized and shaped to be placed in a location proximate to and/or within the vehicle body. In another example, the electronic device 102 may be, or may be a part of, a gaming device that includes a housing sized and shaped to allow a user to participate in an electronic gaming environment. In this example, the wireless transceiver 120 may be sized and shaped to be placed in a location proximate the housing. Further, the gaming device may include a visible interface field defining a visual display configured to visually convey object sensing information to the user, and/or one or more user interfaces positioned proximate the housing, for receiving user input, and in response, conveying object sensing information to the user.

The base station 104 communicates with the electronic device 102 via the wireless link 106, which may be implemented as any suitable type of wireless link. Although depicted as a tower of a cellular network, the base station 104 may represent or be implemented as another device, such as a satellite, cable television head-end, terrestrial television broadcast tower, access point, peer-to-peer device, mesh network node, small cell node, fiber optic line, and so forth. Therefore, the electronic device 102 may communicate with the base station 104 or another device via a wired connection, a wireless connection, or a combination thereof.

The wireless link 106 can include a downlink of data or control information communicated from the base station 104 to the electronic device 102 and an uplink of other data or control information communicated from the electronic device 102 to the base station 104. The wireless link 106 may be implemented using any suitable communication protocol or standard, such as 3rd Generation Partnership Project Long-Term Evolution (3GPP LTE), 5th Generation New Radio (5G NR), IEEE 802.11, IEEE 802.16, Bluetooth™, and so forth. In some implementations, instead of or in addition to providing a data link, the wireless link 106 may wirelessly provide power and the base station 104 may include a power source.

The electronic device 102 includes an application processor 108 and a computer-readable storage medium 110 (CRM 110). The application processor 108 may include any type of processor (e.g., an application processor, a digital signal processor (DSP), or a multi-core processor), that executes processor-executable code stored by the CRM 110. The CRM 110 may include any suitable type of data storage media, such as volatile memory (e.g., random access memory (RAM)), non-volatile memory (e.g., Flash memory), optical media, magnetic media (e.g., disk or tape), and so forth. In the context of this disclosure, the CRM 110 is implemented to store instructions 112, data 114, and other information and software of the electronic device 102. For example, the CRM 110 may include memory for storing data configured to enable the processor/DSP 128 to process object-sensing information against stored data, thereby enabling classification of target objects into different object-type classes. The CRM 110 may reside in the application processor 108, external to the application processor 108, or distributed across multiple entities including the application processor 108. The CRM 110 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

One or more processors 108 may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The electronic device 102 may also include input/output ports 116 (I/O ports 116) and a display 118. The I/O ports 116 enable data exchanges or interaction with other devices, networks, or users. The I/O ports 116 may include serial ports (e.g., universal serial bus (USB) ports), parallel ports, audio ports, infrared (IR) ports, and so forth. The display 118 presents graphics of the electronic device 102, such as a user interface associated with an operating system, program, or application. Alternately or additionally, the display 118 may be implemented as a display port or virtual interface, through which graphical content of the electronic device 102 is presented.

A wireless transceiver 120 of the electronic device 102 may include a wireless transmitter 122 and a wireless receiver 124. The wireless transceiver 120 provides connectivity to respective networks and other electronic devices connected therewith. Additionally, the electronic device 102 may include a wired transceiver, such as an Ethernet or fiber optic interface for communicating over a local network, intranet, or the Internet. The wireless transceiver 120 may facilitate communication over any suitable type of wireless network, such as a wireless LAN (WLAN), peer-to-peer (P2P) network, mesh network, cellular network, wireless wide-area-network (WWAN), and/or wireless personal-area-network (WPAN). In the context of the example environment 100, the wireless transceiver 120 enables the electronic device 102 to communicate with the base station 104 and networks connected therewith.

The wireless transceiver 120 includes circuitry and logic for transmitting and receiving signals via antennas 126. For example, the wireless transceiver 120 may be configured to transmit and/or receive mmW signals via wireless channel, and further, to sense objects relative to, and exterior to, the housing of the electronic device 192 by utilizing mmW signaling. The wireless transceiver 120 may be configured to engage in mmW communication and mmW object sensing substantially simultaneously. Further, the wireless transceiver 120 may be configured to sense objects ranging from about 1 to about 360 degrees, such that the processor/DSP 128 can yield an object-sensing map of objects exterior to the housing of the electronic device 102.

The wireless transceiver 120 includes circuitry and logic for transmitting and receiving signals via antennas 126. Components of the wireless transceiver 120 can include amplifiers, mixers, switches, analog-to-digital converters, filters, and so forth for conditioning signals. The wireless transceiver 120 may also include logic to perform in-phase/ quadrature (I/Q) operations, such as synthesis, encoding, modulation, decoding, demodulation, and so forth. The wireless transceiver 120 may include one or more components or features for adjusting or controlling transmission parameters. For example, the wireless transceiver 120 may provide object-sensing information to the processor DSP 128. In some cases, components of the wireless transceiver 120 are implemented as separate transmitter 122 and receiver 124 entities. Additionally or alternatively, the wireless transceiver 120 can be realized using multiple or different sections to implement respective transmitting and receiving operations (e.g., separate transmit and receive chains). Although the examples described below generally refer to an integrated wireless transceiver 120 that performs both wireless communication and object sensing operations, aspects of the present disclosure are not limited to this case. For example, the electronic device 102 may include an interface circuit for interfacing with an auxiliary and/or auxiliary sensing device, spaced apart from the housing of the electronic device 102. Auxiliary and/or auxiliary sensing devices can include remote wireless devices capable of communicating with the electronic device 102 (e.g., gaming controller, wearable, augmented/virtual reality device, and other types of mobile devices described above). Here, the interface circuit (not illustrated) can enable communication between the electronic device 102 and the auxiliary sensing device, such that the electronic device 102 receives object-sensing information from the auxiliary sensing device. In response to the object-sensing information, the electronic device 102 may moderate a transmission parameter associated with the wireless transceiver 120 transmitting and/or receiving mmW signals. Moderation of transmission power may include controlling and/or modifying transmission power, such as increasing and/or decreasing or otherwise changing transmission power levels.

The electronic device 102 also includes a processor/ digital signal processor (DSP) 128, which is coupled to the wireless transceiver 120. The processor/DSP 128, which may include a modem, can be implemented within or separate from the wireless transceiver 120. Although not explicitly shown, the processor/DSP 128 can include a portion of the CRM 110 or can access the CRM 110 to obtain computer-readable instructions. The processor/DSP 128 controls the wireless transceiver 120 and enables wireless communication or proximity detection to be performed. For example, the processor/DSP 128 may control a power amplifier at the transceiver 120 to moderate a transmission parameter based on object-sensing information. The processor/ DSP 128 can include baseband circuitry to perform high-rate sampling processes that can include analog-to-digital conversion, digital-to-analog conversion, Fourier transforms, gain correction, skew correction, frequency translation, and so forth. The processor/DSP 128 can provide communication data to the wireless transceiver 120 for transmission. The processor/DSP 128 can also process a baseband version of a signal obtained from the wireless transceiver 120 to generate data, which can be provided to other parts of the electronic device 102 via a communication interface for wireless communication or proximity detection.

In some examples, the electronic device 102 (e.g., via the processor/DSP 128) may be configured to generate, output, or produce a map. A map can be based at least on the object-sensing information. A map can include spatial location and other information associated with objects surrounding the electronic device 102 (e.g., communication status, operational status, relative object location, direction, movement, type and/or class). In addition, a map can be used to display and/or identify objects, humans, and/or animals relative to the electronic device 102. A map may be time static or may be time dynamic. A map can be used to visually display objects around a device ranging from a full 360-degree arrangement as well as other or smaller ranges (e.g., from about 1 degree to about 360 degrees). A map can enable a user to access an augmented/virtual reality environment (e.g., (e)gaming, (tele)health, and/or educational). According to some aspects, a map may be provided as an output to a user via a display screen (e.g. display screen shown for electronic device 102) or other user interface. The electronic device 102 may transmit map information to other devices in the network. According to some aspects, sharing map information in this manner can aid in spreading map and/or spatial positioning information within a network.

Although not explicitly depicted, the wireless transceiver 120 or the processor/DSP 128 can also include a controller. The controller can include at least one processor and at least one CRM, such as the application processor 108 and the CRM 110. The CRM can store computer-executable instructions, such as the instructions 112. The processor and the CRM can be localized at one module or one integrated circuit chip or can be distributed across multiple modules or chips. Together, a processor and associated instructions can be realized in separate circuitry, fixed logic circuitry, hard-coded logic, and so forth. The controller can be implemented as part of the wireless transceiver 120, the processor/DSP 128, a special-purpose processor configured to perform MPE techniques, a general-purpose processor, some combination thereof, and so forth.

The processor/DSP 128 may include feature extraction circuitry 130 and SVM classification circuitry 132. The feature extraction circuitry 130 may be utilized for extracting features of a reflection signal, indicative of micromovements characteristic of a human target. The SVM classification circuitry 132 may be utilized for determining a category or classification of a target object, based on one or more extracted features of the reflection signal. For example, the SVM classification circuitry 132 may apply the extracted features to a classification model, wherein the SVM classification circuitry 132 determines a location of the target object, within a feature space, relative to a boundary that separates objects within the feature space into categories. Based on this location, the SVM classification circuitry 132 may identify the category of the target object, including human tissue, non-human objects, or a combination thereof.

In some examples, the base station 104 may be a data store, or may be in communication with one or more data stores that receive micromovement information from wireless communication devices via the wireless network. In this manner, a data store may communicate object classification information between wireless communication devices in the network. Based on this information, the data store may determine object class information for one or more target objects based at least in part on received micromovement information and, in some examples, other stored information. This object class information may then be communicated to other wireless communication devices such that any one of the wireless communication devices in the network can moderate a wireless transmission parameter associated with its transmission and reception operations. In a further example, the data store may communicate information indicating that any one or more of the wireless communication devices has moderated its power transmission levels, e.g., based on target object classification.

Figure 2:
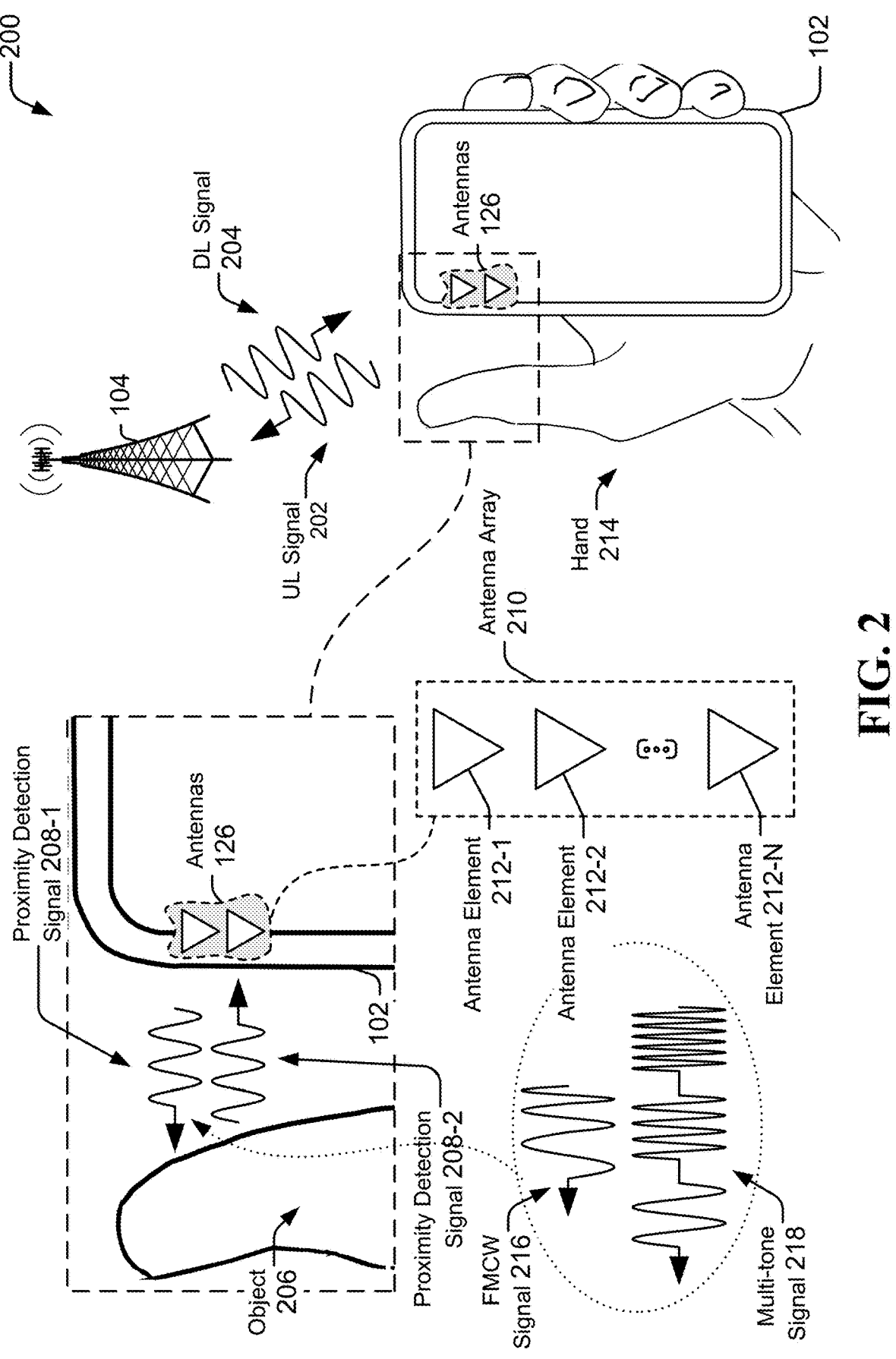
FIG. 2 is a schematic diagram of an operating environment for an electronic device utilizing a radar-based proximity detector according to some aspects of the disclosure.

FIG. 2 illustrates an example operating environment 200 for categorizing target objects detected utilizing a radar based proximity detector. In the example environment 200, a hand 214 of a user holds the electronic device 102. In one aspect, the electronic device 102 communicates with the base station 104 by transmitting an uplink signal 202 (UL signal 202) or receiving a downlink signal 204 (DL signal 204) via at least one of the antennas 126. A user's thumb, however, may represent a proximate target object 206 that may be exposed to radiation via the uplink signal 202. To determine a range to the target object 206, the electronic device 102 transmits a proximity detection signal 208-1 via at least one of the antennas 126 and receives a reflected proximity detection signal 208-2 via at least another one of the antennas 126.

In one implementation, the proximity detection signal 208-1 includes a frequency-modulated continuous-wave (FMCW) signal 216. In general, a frequency of the FMCW signal 216 increases or decreases across a time interval. Different types of frequency modulations may be used, including linear-frequency modulations (LFM) (e.g., chirp), sawtooth-frequency modulations, triangular-frequency modulations, and so forth. The FMCW signal 216 enables radar-based ranging techniques to be utilized to determine the range to the target object 206. To achieve a finer range resolution (e.g., on the order of centimeters (cm)) for close-range applications, larger bandwidths can be utilized, such as 1 gigahertz (GHz), 4 GHz, 8 GHz, and so forth. For instance, the FMCW signal 216 can have a bandwidth of approximately 4 GHz and include frequencies between approximately 26 and 30 GHz. The finer range resolution improves range accuracy and enables multiple objects 206 to be distinguished in range. The FMCW signal 216 can provide an accurate range measurement for a variety of distances based on the bandwidth (e.g., between approximately 4 and 20 cm for a 4 GHz bandwidth). An amount of time for performing proximity detection can also be relatively short using the FMCW signal 216, such as within approximately one microsecond.

In another implementation, the proximity detection signal 208 may be a multi-tone signal 218, which includes at least three tones (e.g., frequencies). The multi-tone signal 218 can be generated using existing components within the wireless transceiver 120, which are also used to generate the uplink signal 202. For example, the multi-tone signal 218 can be generated using an existing phase lock loop (PLL), using Orthogonal Frequency-Division Multiplexing (OFDM), or using a multi-tone transmit signal generated at baseband via a digital signal generator. Depending on the technique used, an amount of time for performing proximity detection via the multi-tone signal 218 can be on the order of approximately one microsecond and 400 microseconds. Frequency separations between the tones can be on the order of megahertz (MHz) or GHz. A bandwidth of the multi-tone signal 218 can be, for example, approximately 800 MHz or 2 GHz. The range to the object 206 is determined by analyzing a change in phase across each of these tones. To improve range accuracy, larger bandwidths (e.g., separations between tones) or larger quantities of tones can be used. The multi-tone signal 218 can be used to measure ranges between approximately 0 and 7 cm.

In some electronic devices 102, the antennas 126 may include at least two different antennas, at least two antenna elements 212 of an antenna array 210, at least two antenna elements 212 associated with different antenna arrays 210, or any combination thereof. As shown in FIG. 2, the antennas 126 correspond to the antenna elements 212 within the antenna array 210, which can include multiple antenna elements 212-1 to 212-N, where N represents a positive integer. Using at least one of the antenna elements 212, the wireless transceiver 120 can transmit the proximity detection signal 208-1 while receiving the reflected proximity detection signal 208-2 using at least another one of the antenna elements 212. In other words, the wireless transceiver 120 can receive the reflected proximity detection signal 208-2 via a first antenna element 212-1 during a portion of time that the proximity detection signal 208-1 is transmitted via a second antenna element 212-2. The antennas 124 and/or elements thereof may be implemented using any type of antenna, including patch antennas, dipole antennas, and so forth.

If the electronic device 102 includes multiple antennas 126 located on different sides of the electronic device 102 (e.g., a top, a bottom, or opposite sides), the described techniques can enable the user to be detected with respect to each antenna 126. In this way, transmission parameters can be independently adjusted relative to the range of the object 206 with respect to each antenna 126. Such independent detection therefore enables the two or more of the antennas 126 to be configured for different purposes. For example, one of the antennas 126 can be configured for enhanced communication performance while another one of the antennas 126 is simultaneously configured to comply with FCC requirements. As described in further detail with respect to FIG. 3, some of the components of the wireless transceiver 120 can be utilized for both wireless communication and proximity detection, either at different times or simultaneously. In some examples, the electronic device may perform radar sensing and proximity detection during unused time slots of a wireless communication protocol. For example, in mmW communication, a communication frame may include one or more unused slots for random channel access (RACH); the electronic device 102 may perform radar sensing and proximity detection during these otherwise unused RACH slots.

In some examples, when the electronic device 102 is operating in a wireless communication network, the electronic device 102 may communicate object sending data to one or more other devices within the network. In this manner, the electronic device 102 and the other devices can share target object sensing data with one another. Accordingly the electronic device 102 and the other devices may determine surrounding target object information of objects located around them.

Figure 3:
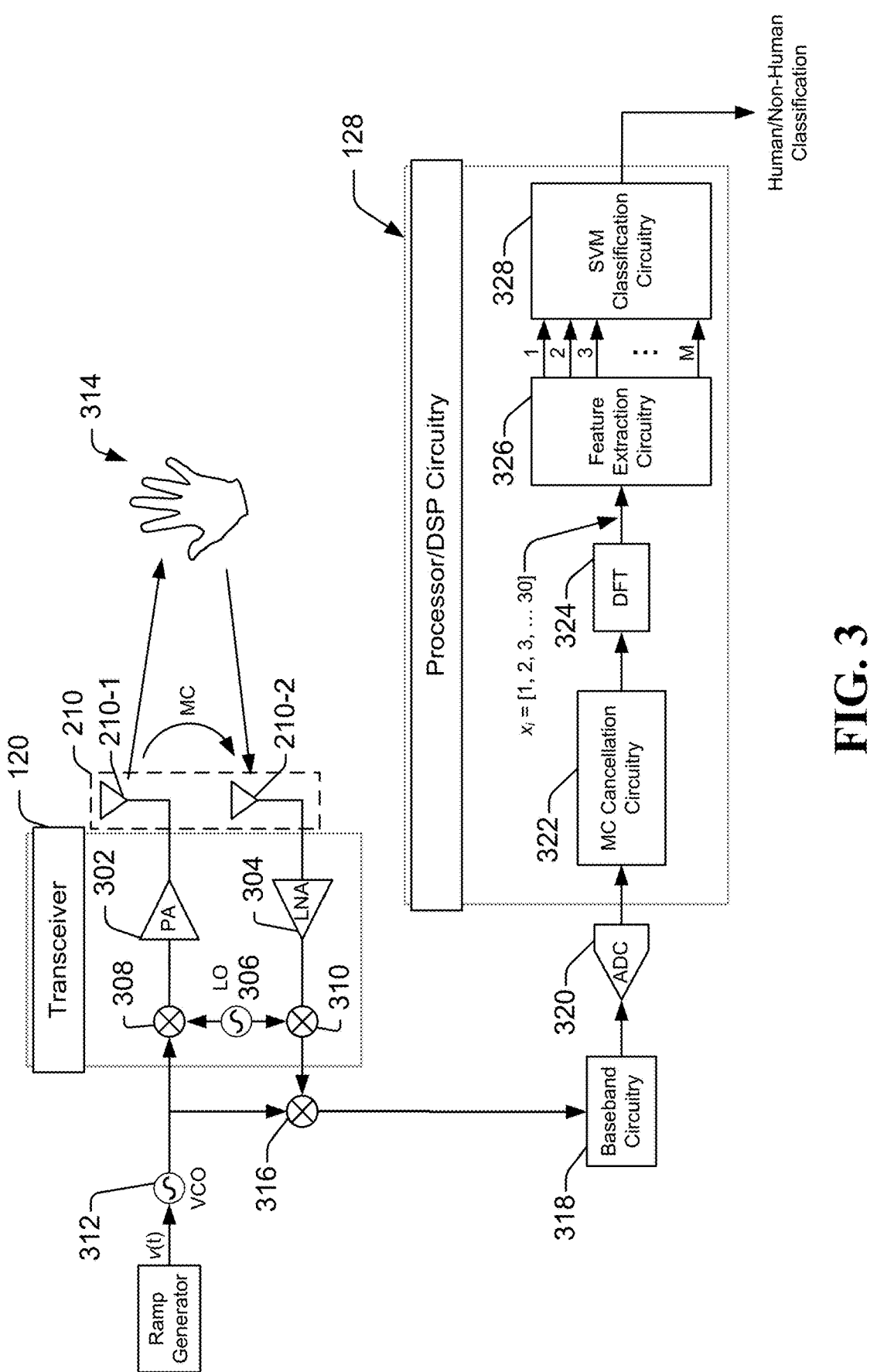
FIG. 3 is a block diagram illustrating additional detail of a portion of an electronic device according to some aspects of the disclosure.

FIG. 3 illustrates an example implementation of a wireless transceiver 120 and processor/DSP circuitry 128 for a machine learning (ML) algorithm to categorize target objects detected utilizing a radar-based proximity detector according to some aspects of this disclosure. The wireless transceiver 120 may include a transmitter 122 and a receiver 124, which are respectively coupled between the processor/DSP 128 and an antenna array 210. The transceiver 120 includes a power amplifier (PA) 302 configured to dynamically provide power to selected ones of the antenna elements 210 for moderation of the transmission parameter and/or for beamforming. The transceiver 120 further includes a low-noise amplifier (LNA) 304 for amplifying a signal received by a receive antenna 210-2. Local oscillator (LO) circuitry 306 is coupled to mixers 308 and 310. The LO circuitry 306 generates at least one reference signal, which enables the mixers 308 and 310 to upconvert or downconvert analog signals within the transmit or receive chains, respectively. The LO circuitry 306 may further be configured to generate one or more different types of reference signals to support both proximity detection and wireless communication. In some examples, the LO circuitry 306 may be configured to generate one or more in-phase and quadrature (I/Q) reference signals. In this manner, the transmission from the transmit antenna 210-1 may include I and Q components. And further, after the reflected signal is received from the receive antenna 210-2, I and Q components of the reflected signal may be separated from one another for processing.

The transceiver 120 can also include other additional components that are not depicted in FIG. 3. These additional components can include band-pass filters, additional mixers, switches, and so forth. Moreover, as discussed above, the transceiver 120 may be configured not only for the target object ranging and detection described immediately below, but additionally for wireless communication.

Although not explicitly depicted, the wireless transceiver 120 and/or the processor/DSP 128 can also include a controller. The controller can include at least one processor and at least one CRM, such as the application processor 108 and the CRM 110. The CRM can store computer-executable instructions, such as the instructions 112. The processor and the CRM can be localized at one module or one integrated circuit chip or can be distributed across multiple modules or chips. Together, a processor and associated instructions can be realized in separate circuitry, fixed logic circuitry, hard-coded logic, and so forth. The controller can be implemented as part of the wireless transceiver 120, the processor/DSP 128, a special-purpose processor configured to perform MPE techniques, a general-purpose processor, some combination thereof, and so forth.

A voltage-controlled oscillator (VCO) 312 may be configured to generate a sinusoidal signal having a frequency that depends on a voltage of an input signal v(t). That is, by properly varying the input signal v(t) to the VCO 312, the VCO 312 may generate, for example, a sinusoid of increasing frequency over time, often called a chirp signal. This chirp signal can be utilized for an FMCW-based radar. Of course, other suitable input signals v(t), and other suitable radar configurations may be utilized within the scope of this disclosure for proximity detection and target object sampling.

The chirp signal may be amplified by the PA 302 and mixed with the LO signal (i.e., upconverted) at the mixer 308 for transmission from a transmit antenna 210-1. The transmitted signal may reflect off a target object 314, being reflected back to a receive antenna 210-2. The reflected signal at the receive antenna 210-2 may be mixed with the LO signal (i.e., downconverted) at the mixer 310 and amplified by the LNA 304.

The output of the LNA 304 (i.e., the amplified received signal) may be mixed with the chirp signal at a mixer 316. With an FMCW-based radar, this mixing creates a beat signal, which is representative of a frequency offset between the radio-frequency transmit signal and the radio-frequency receive signal. In general, the frequency of the beat signal is proportional to the distance of the target object 314.

The beat signal may be processed by baseband circuitry 318, configured to perform various baseband functions including but not limited to gain correction, skew correction, frequency translation, etc. The output from the baseband circuitry 318 may be converted to the digital domain utilizing one or more analog-to-digital converters (ADC) 320. In an example wherein the radar transmission includes I and Q components, as discussed above, the output from the baseband circuitry 318 may include separate I and Q signals, and the ADC 320 may include two ADCs for respectively converting each of the I and Q components to the digital domain. The digital output from the ADC 320 may then be provided to the processor/DSP circuitry 128. In some implementations, the processor/DSP circuitry 128 may be a DSP or any suitable functional component for carrying out the below-described processes.

An undesired side effect of having a closely located transmit antenna 210-1 and receive antenna 210-2, as may occur in a small electronic device, is mutual coupling (MC). That is, part of the transmitted energy may couple back to the receiver. This mutual coupling is a well-known issue in the art. Within the processor/DSP circuitry 128, MC cancellation circuitry 322 may provide cancellation of the undesired energy coupled between the transmit antenna 210-1 and the receive antenna 210-2. To remove the MC component from the received signal, the MC cancellation circuitry 322 uses the transmit signal to cancel the MC component. Although not explicitly shown, the MC cancellation can be performed in a time domain or a frequency domain via the MC cancellation circuitry 322.

After cancelling the MC, discrete Fourier transform (DFT) circuitry 324 may convert the received beat signal to the frequency domain and provide samples of the beat signal in this domain. For example, if 30 measurements of the target object 314 are obtained from 30 sequential target object reflections, the output x from the DFT circuitry 324 includes $x_i=[x_1, x_2, \ldots, x_{30}]$ as its output. Here, each sample $x_i$ corresponds to a spectrum measured from a single radar reflection. These samples $x_i$ may then be sent to feature extraction circuitry 326. That is, according to an aspect of this disclosure, one or more features (e.g., M features, as shown in the illustration) may be extracted from the spectra of a sequence of radar samples of a target object 314. The extracted features may be utilized for classifying the target object as human or non-human, for example, as described further below. That is, features indicative of micromovements characteristic of human target objects may be utilized for categorization of the target object as such.

The M extracted features may then be provided to classification circuitry 328. In some examples, the classification circuitry 328 may be a support vector machine (SVM) that utilizes machine learning (ML) to classify target objects. As described further below, SVM classification circuitry 328 may determine distances of the extracted features with respect to a boundary in a defined feature space. Based on the distances from, and/or the location relative to such a boundary in the defined feature space, the SVM classification circuitry 328 may then provide a determination of a categorization of the target object 314, e.g., as human or non-human. Also as described further below, based on the categorization of the target object 314, the processor/DSP circuitry 128 can generate a transmission parameter that controls one or more transmission attributes for wireless communication. By specifying the transmission parameter, the processor/DSP circuitry 128 can, for example, cause the transceiver 120 to decrease a transmit power if a target object 314 that is near the electronic device 102 is a human, or increase the transmit power if the target object 314 is farther away from the electronic device 102 and/or is not a human. For example, the power amplifier 302 may be dynamically controlled based on the target object classification. If the target object 314 is determined to not be human, the processor 122 can, for example, keep the transmission parameter unchanged. The transmission parameter can adjust a power level, a beam steering angle, a frequency, a selected antenna or antenna array, or a communication protocol that is used to transmit an uplink signal and/or receive a downlink signal. The ability to determine the range to the target object 314 and the category of the target object 314, and to control the transceiver 120, enables the processor 122 to balance performance of the electronic device 102 with compliance or radiation requirements.

The processor/DSP circuitry 128 may also be coupled to the LO circuitry 306, which can enable the processor/DSP circuitry 128 to control the LO circuitry 306 via a mode signal. The mode signal, for example, can cause the LO circuitry 306 to switch between generating reference signals for proximity detection or generating reference signals for wireless communication. In other implementations, the application processor 108 (see FIG. 1) can perform one or more of these functions.

Although the wireless transceiver 120 is shown as a direct-conversion transceiver in FIG. 3, the described techniques can also be applied to other types of transceivers, such as superheterodyne transceivers. In general, the LO circuitry 306 can be used to perform frequency conversion between any frequency stage (e.g., between baseband frequencies and radio frequencies, between intermediate frequencies and radio frequencies, or between baseband frequencies and intermediate frequencies).

Figure 4:
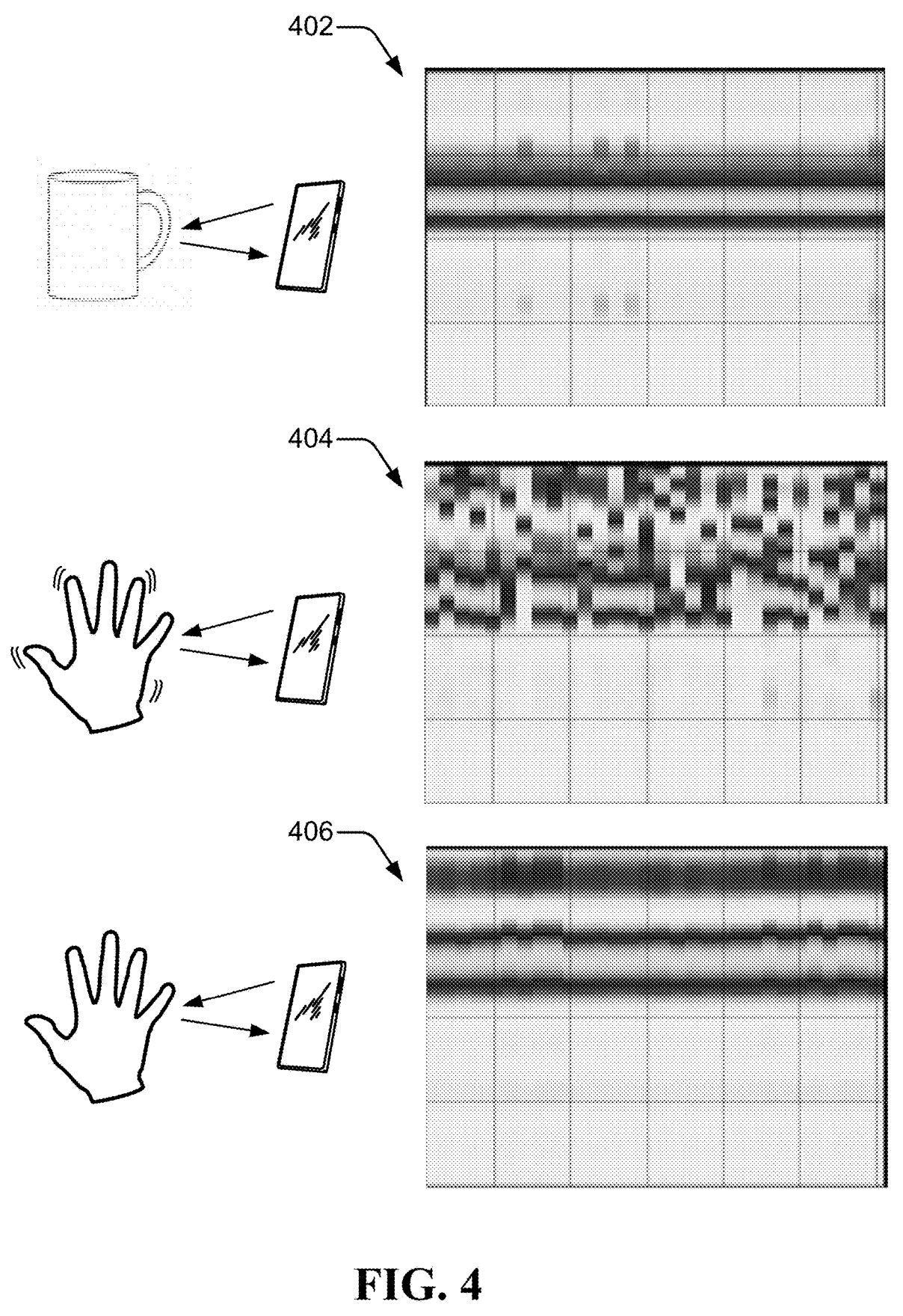

FIG. 4 illustrates a series of three charts generated utilizing an exemplary implementation of an electronic device 102. Each illustrated chart shows data from 30 consecutive captures of reflected radar pulses over a period of 9 seconds, with samples captured at an interval of 0.3 seconds. In each respective chart, the horizontal axis represents time (or sample index), and the vertical axis represents the distance from the electronic device, as determined utilizing the range detection algorithm generally described above. Further, the shade at any given point represents the energy content of the received signal reflected off the target object at the corresponding time and distance from the electronic device. For example, the feature extraction circuitry 326 may determine the parameters, including the energy content of the received signal at each target range, among other parameters.

Chart 402 provides a data set corresponding to a stationary, non-human target object, such as a coffee mug. As shown, such a static, stationary target object is characterized by a relatively static data across samples. Chart 404 illustrates a data set corresponding to a moving human hand as a target object. This exhibits significant variations in the data over time. And chart 406 illustrates a data set corresponding to a human hand as a target object, where the person is holding their hand stationary. Even when a person attempts to hold perfectly stationary, they cannot eliminate micromovements caused by to small muscular movements, breathing, vascular pulse, etc. Because an integrated FMCW-based radar utilizing mmW spectrum has wavelengths on the order of 1 cm or smaller, it is capable of detecting very small movements, such as 2 or 3 mm, in a target object.

By observing data from various objects such as these, the inventors recognized that when the detected target object is of a human nature, the observed data exhibit variations or fluctuations of a variety of metrics or features, such as the peak energy of the reflected signal, side lobe variations, etc. And furthermore, by analyzing these fluctuations over a suitable set of features extracted from a target object, the target object can reliably and accurately be categorized as either a human or non-human target object. According to various aspects of the present disclosure, a machine learning (ML) algorithm is provided for utilizing these and other features to categorize target objects. In this manner, in some examples transmission characteristics may be controlled to dynamically meet MPE requirements for mmW transmissions.

FIG. 5 provides two charts illustrating exemplary 2-dimensional (2D) feature spaces. These charts provide examples for how the use of suitable sets of extracted features can be combined to improve the reliability of categorizing target objects detected with a radar-based proximity detector as described above. In the context of the present disclosure, a feature refers to a determined parameter that is relevant or specific to the issue of classification of target objects. That is, an electronic device 102 may extract one or more features to determine whether a target object is human.

In the charts shown in FIG. 5, each point corresponds to a data sample collected from measurements of a target object, post-processing. In the first chart 502, the horizontal axis represents the variance, over 30 sequential radar reflections, of the peak power less the average power of the reflected signal. The vertical axis represents the maximum of the discrete Fourier transform (DFT) of the power of the reflected signal less the average of the DFT of the power of the reflected signal. And in the second chart 504, the horizontal axis represents the mean, over 30 sequential radar reflections, of the change ($\Delta$) in phase between sample n and sample n−1; and the vertical axis represents the variance of the change ($\Delta$) in phase between sample n and sample n−1.

In each of these charts, each 'x' represents a data point from a human target object, and each '○' represents a data point from a non-human target object. As can clearly be seen, the circles '○' representing samples of non-human target objects form a cluster on the lower left corner. On the other hand, the 'x'es representing samples of human target objects are spread across the chart. Thus, in these exemplary illustrations, a simple linear boundary separation might be used to distinguish between the human and non-human samples.

Figure 6:
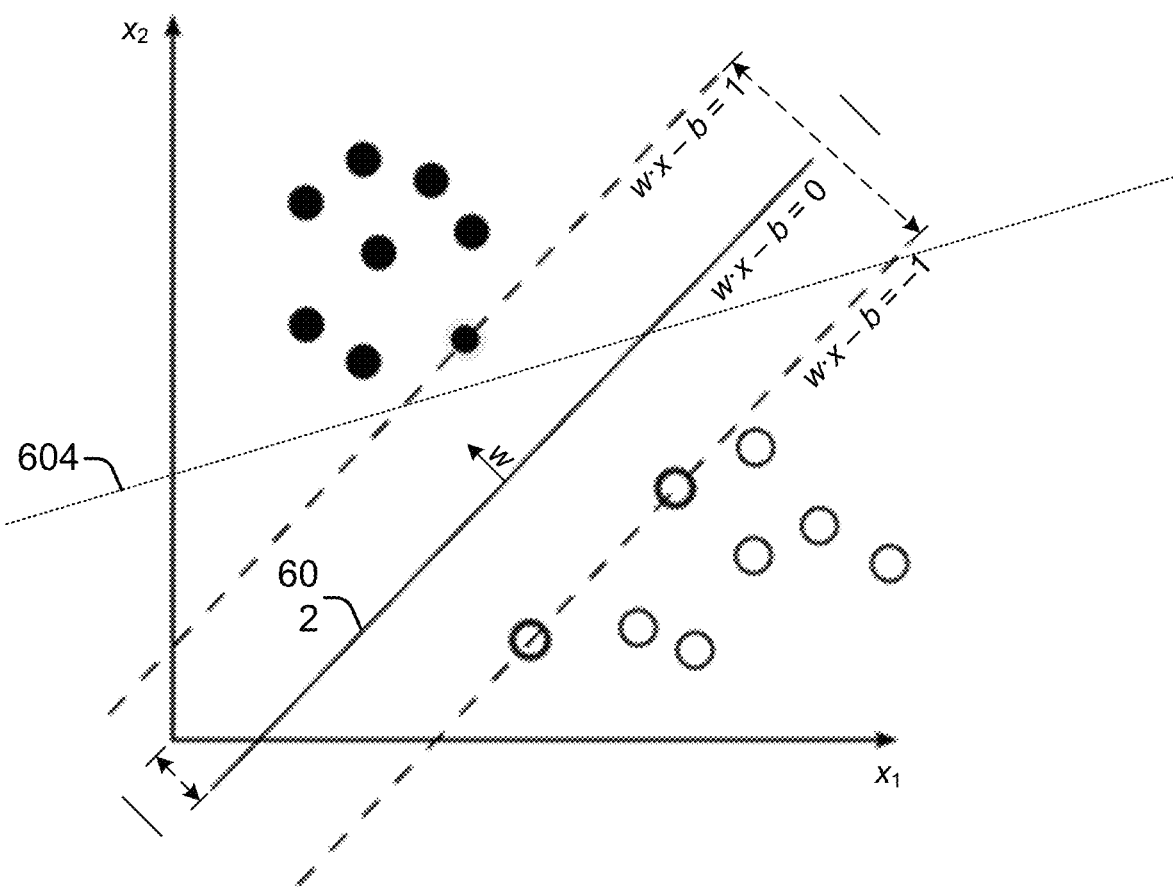
FIG. 6 is a chart showing how a service vector machine (SVM) can establish an optimal boundary separating different categories of target objects according to some aspects of the disclosure.

FIG. 6 illustrates a further example of a 2D feature space showing one example of how a classifier algorithm can utilize data from target objects of known classification to determine an optimal separation between target objects of different categories. In this illustration, the axes labeled $x_1$ and $x_2$ represent features extracted from the target objects. The data points shown with the filled-in circle (•) each correspond a human target object, and the data points shown with an empty circle (○) each correspond a non-human target object.

The charts in FIGS. 5 and 6 show a 2D feature space, comparing two extracted features to obtain a categorization between human and non-human target objects. However, aspects of this disclosure are not limited to such a 2D feature space. In general, due to higher dimensionality of the feature space, a many-dimensional comparison between any suitable number of features may be constructed. In such a case, rather than the line 602 being the boundary between classes, a plane or a hyper plane may be utilized to separate the classes of target objects within a higher-dimensional feature space. That is, an exemplary classification circuitry 328 may utilize an SVM to analyze any suitable number of extracted features from a set of samples from a target object and determine that target object's classification.

Referring again to FIG. 6, it may be observed that the different categories of data points can easily be separated from one another. However, for optimal separation of the different categories to most reliably categorize new data from target objects in the future, a categorization model should identify the best separation between the categories. For example, an infinite number of lines, such as the line 602, could theoretically fully separate the measurements in the given data set. However, if a categorization model were to utilize the illustrated line 604 to predict the category of future target objects, the prediction may be unreliable. That is, because the line 604 passes close to the cluster of measured human target objects, even small variations in the extracted features of a future measurement of a human target object could cause the measurement to fall on the opposite side of the line 604, resulting in the model miscategorizing the target object.

In an aspect of this disclosure, a machine learning (ML) algorithm may be utilized to establish a reliable separation between sets of target objects into distinct categories, e.g., human and non-human target objects. That is, a classifier algorithm may be established by building a large dataset (e.g., training data) including many human body parts (e.g., hands in different poses, arms, faces, etc.) as well as many non-human objects commonly encountered by electronic devices.

As one example, the classification circuitry 328 may be a support-vector machine (SVM), which may be utilized to build a target object classifier algorithm. SVMs are ML models well-known in the art used for classification of data sets. Broadly, an SVM may be utilized to analyze a data set and identify a boundary between classes, by maximizing the minimum distance between the closest point in each class's set of samples, and the boundary. These boundaries are called support vectors.

Referring once again to FIG. 6, the chart shows data corresponding to eight realizations of human target objects (•), and eight realizations of non-human target objects (○). Here, a realization corresponds to a set of radar captures or observances received after reflecting off a target object, based on a radar transmission. According to an aspect of the present disclosure, by virtue of selection of suitable features $x_1$ and $x_2$ extracted from each realization, it can be observed that the two classes of data can be separated into distinct groups. In a further aspect, the classification circuitry 328 (e.g., an SVM) can be utilized to calculate, based on these data, the optimal boundary between the classes.

As discussed above, in a 2-dimensional feature space as illustrated in FIG. 6, the boundary corresponds to a line. In an aspect of this disclosure, this line may be represented by the values where $wx-b=0$. Here, w is a weight vector; x is a vector $\langle x_1, x_2 \rangle$ within the feature space; and b is a scalar bias or offset. In this equation, the weight vector w is configured such that the product of the two vectors wx results in a scalar value.

As seen in FIG. 6, in the 2-dimensional feature space, the separation between lines that are parallel to the boundary 602, which cross through the closest samples in each class, has the value of $$\frac{2}{\|w\|}.$$

The boundary 602 may be selected to be centered between these respective lines. Here, $\|w\|$ represents the norm of w, calculated as the root of the sum of the squares of all elements of the vector (in the illustrated case, $\|\|w\|\|=\sqrt{x_1^2+x_2^2}$). And as further seen in FIG. 6, $$\frac{b}{\|w\|}$$

is the distance or offset of the boundary 602 from the origin.

The classification circuitry 328 (e.g., an SVM), based on analysis of the data set, determines the values of w and b for the optimal boundary 602 between the classes based on the training data given to it. That is, although this illustration shows a total of 16 samples or realizations, with 8 each from human target objects and non-human target objects, any suitable number of samples may be utilized as a training data set. In general, the larger and more diverse/varied in nature the training data used, the more reliable will be the calculated boundary 602 for determining the class of new incoming samples.

In general, the classification circuitry 328 may generate a boundary (e.g., a line, a plane, or a hyperplane, depending on the number of dimensions in the feature space) to separate samples from different categories. That is, the SVM defines a boundary that separates the samples from the different categories such that the minimum distance between samples in each category and the boundary is maximized. With this boundary, a robust way to distinguish the different categories can be provided.

By having such a boundary predetermined, the computational cost for the electronic device 102 to categorize a new target object can be reduced. That is, a deep learning algorithm or a neural network algorithm could potentially determine a separation between categories in real time. However, the use of such an algorithm would come at the cost of high computational requirements, high power usage, a long time for computation, and even a higher system expense.

The following provides some examples of features that may be useful for distinguishing a human target object from a non-human target object. According to an aspect of this disclosure, feature extraction circuitry 326 may analyze a set of realizations (reflected signals) from a target object as described above to extract a set of M features corresponding to that target object.

In some examples, feature extraction circuitry 326 may utilize dynamic time warping (DTW). DTW is an algorithm known in the art for determining the similarity between sequences (e.g., sequences X and Y, each having L samples), and is defined according to the equation:

$$DTW(X, Y) = \min\left\{\sum_{l=1}^{L} c\left(x_{n_l}, y_{m_l}\right)\right\}$$

where $X=\{x_1, x_2, \ldots, x_L\}$, and $Y=\{y_1, y_2, \ldots, y_L\}$. Thus, for each sample in X and each sample in Y, the DTW relies on a comparison of the distance between the respective values in the DFT domain. In general, the DTW of two very similar sequences may be very small, whereas the DTW of two very different sequences may be large.

$$1. \ \mathrm{Var}_{DTW} = \mathrm{var}_{n}(DTW_n)$$

For example, a feature that the feature extraction circuitry 326 may extract is the variance of the DTW ($\mathrm{Var}_{DTW}$) over a series of realizations (e.g., a series of 10, or any suitable number of realizations). In the equation above, $\mathrm{Var}_{DTW}$ corresponds to the variance, across n realizations, of the calculated DTW. For a static (e.g., non-human) object, the variance of the determined DTW over a series (e.g., a series of 10) of realizations will be very small, as each realization will provide essentially the same data. On the other hand, for a human target object, a series (e.g., a series of 10) of realizations will have noticeable differences from one another, due to movements or micromovements of the human target object. Therefore, the variance of the DTW across the series of realizations would be greater than that for non-human target objects.

$$2. \ \mathrm{Max}_{DTW} = \max_{n}(DTW_n)$$

In a further example, a feature that the feature extraction circuitry 326 may extract is the maximum of the DTW ($\mathrm{Max}_{DTW}$) over a series of realizations (e.g., a series of 10, or any suitable number of realizations). In the equation above, $\mathrm{Max}_{DTW}$ corresponds to the maximum, across n realizations, of the calculated DTW. Here, the maximum of the DTW may be considered as a spread between different realizations. By utilizing the maximum DTW, even if a human target object is fairly stable for, for example, 5 realizations, but then exhibits motion, an electronic device can determine that the maximum DTW is relatively high. Accordingly, even for a temporarily very stationary target object, strong movements can be utilized to categorize a target object as human.

$$3. \ \mathrm{Var\_}\Delta P_{avg\_max} = \max_{i}\left\{\sum_{n}\mathrm{Var}\left[\Delta P_{avg_{peaks}}(i, n)\right]\right\}$$

In a further example, a feature that the feature extraction circuitry 326 may extract is the variance of the difference between the peak power in each realization, and the average peak power across a sequence of realizations. For example, after DFT circuitry 324 may calculate the DFT for a given realization. This DFT can provide the received power of that sample at each of a range of frequencies. In an example utilizing FMCW-based radar, these frequencies correspond to the distance from the electronic device. Accordingly, by plotting the power P vs. the distance, one or more local maxima or peaks (e.g., i local maxima) may appear for each respective sample. In this extracted feature, across multiple realizations, an average peak value may be determined. Here, the change ($\Delta$) in the detected peak power level for each sample n relative to the average peak value may be determined; and across multiple realizations, the variance of this change may be determined. According to an aspect of this disclosure, the value of this feature may be higher for a human target object than for a non-human target object.

$$4. \ \mathrm{Var\_}\Delta D_{peaks\_max} = \max_{i}\left\{\sum_{n}\mathrm{Var}[\Delta D_{peaks}(i, n)]\right\}$$

In a further example, a feature that the feature extraction circuitry 326 may extract is the variance of the difference between the distance where the peak power lies in each realization, and the average distance where the peak power lies across a sequence of realizations. This feature is very similar to that described above for $\mathrm{Var\_}\Delta P_{avg\_max}$. However, here, rather than looking at the measured power, this feature looks at the measured distance from where that peak power was captured. Similar to the above, the value of this feature may be higher for a human target object than for a non-human target object.

$$5. \ \Delta DFT_{peak} = \max_{n}\left(DFT_{peak\_pwr_n}\right) - \min_{n}\left(DFT_{peak\_pwr_n}\right)$$

In a further example, a feature that the feature extraction circuitry 326 may extract is the spread ($\Delta$) of the peak power of the DFT of a realization, over a series of n (e.g., a series of 10) realizations. That is, as shown in equation 5 above, the spread is defined as the difference between the maximum (max) peak power of the DFT and the minimum (min) peak power of the DFT across the series of realizations. With a stationary non-human target object, this spread would be expected to be relatively small, while with a human target object, exhibiting at least micromovements, this spread would be expected to be larger.

$$\mathrm{Var\_DFT}_{peak} = \mathrm{Var}\left(DFT_{peak\_pwr_n}\right) \qquad 6.$$

In a further example, a feature that the feature extraction circuitry 326 may extract is the variance of the peak power of the DFT across a series of n (e.g., a series of 10) realizations. With a stationary non-human target object, this variance would be expected to be relatively small, while with a human target object, exhibiting at least micromovements, this variance would be expected to be larger.

$$7. \ \mathrm{Var\_}\Delta P_{b2b_{peaks}} = \max_{i}\left\{\sum_{1}^{n-1}\mathrm{Var}\left[\Delta P_{avg_{peaks}}(i, n)\right]\right\}$$

In a further example, a feature that the feature extraction circuitry 326 may extract is the variance of the change ($\Delta$) in the power measured in consecutive captures. In equations 1-6 above, the extracted features have relied on relationships across full sequences of realizations. However, in equation 7 (and equation 8, below), the extracted features rely on relationships between consecutive or sequential individual captures or realizations. When a target object is human, due to the micromovements that may occur at any given time, there may be relatively large changes in the peak power from one capture to the next. By utilizing the variance of this parameter as an extracted feature, micromovements characteristic of a human target object can be identified.

$$8.\ \text{Var\_}\Delta D_{b2b_{peaks}} = \max_i \left\{ \sum_1^{n-1} \text{Var}\left[\Delta D_{avg_{peaks}}(i,n)\right] \right\}$$

In a further example, a feature that the feature extraction circuitry 326 may extract is the variance of the change ($\Delta$) in the distance at which the peak power occurs in consecutive or sequential captures or realizations. When a target object is human, due to micromovements that may occur at any given time, there may be relatively substantial changes in the peak power distance from one capture to the next. By utilizing the variance of this parameter as an extracted feature, micromovements characteristic of a human target object can be identified.

In some further examples, the feature extraction circuitry 326 may extract features based on the in-phase and quadrature (I/Q) samples in the time domain after removal of the mutual coupling. As one example, a sequence of n consecutive time domain samples (e.g., 10 samples) may be collected utilizing an FMCW-based radar as described above. The real part of the time domain samples may be determined according to the following equation:

$$\text{Re}\{IQ_{avg}\} = \left(\frac{1}{n}\sum_n \text{Re}\{IQ_n\}\right)$$

And further, the imaginary part of the time domain samples may be determined according to the following equation:

$$\text{Im}\{IQ_{avg}\} = \left(\frac{1}{n}\sum_n \text{Im}\{IQ_n\}\right)$$

When collecting samples of a human target object, even in the time domain there may be 'noise' or variations in the measured power of consecutive samples due, e.g., to micromovements. However, when collecting samples of a stationary non-human target object the measured power of consecutive samples may generally be relatively stable. Accordingly, an electronic device 102 can utilize calculated parameters such as the variance of the time domain samples to categorize target objects. In a further example, the mean value of the I/Q samples may be removed (mean removal). For example, the calculated average or mean across a set of samples may be subtracted from the value of each sample. In this way, any bias or offset that might impact the final result can be accounted for.

$$9.\ \text{Var}\left\{\frac{1}{n}\sum_n \left[(\text{Re}(IQ_n) - \text{Re}(IQ_{avg})\right]\right\}$$

Thus, in one example, a feature that the feature extraction circuitry 326 may extract is the variance (Var{ }) of the real part (Re( )) of the time domain samples ($IQ_n$), with mean removal as described above.

$$10.\ \text{Var}\left\{\frac{1}{n}\sum_n \left[(\text{Im}(IQ_n) - \text{Im}(IQ_{avg})\right]\right\}$$

In a further similar example, a feature that the feature extraction circuitry 326 may extract is the variance of the imaginary part (Im( )) of the time domain samples, with mean removal as described above.

FIG. 7 is a flow chart illustrating an exemplary process for building a human target object classifier in accordance with some aspects of the present disclosure. In various examples, some or all illustrated features may be omitted in a particular implementation within the scope of the present disclosure. Further, some illustrated features may not be required for implementation of a particular example. In some examples the process in FIG. 7 may be carried out by a manufacturer, vendor, or retailer of the electronic device 102. In some examples, the process in FIG. 7 may be carried out by any suitable apparatus or means for carrying out the functions or algorithm described below.

At block 702, a data collection process may be carried out. For example, an electronic device 102 may collect a data set of radar captures on multiple humans, for example of different gender, ethnicity, age, size, etc. These data may be collected from various body parts of the subject people. Further, the electronic device 102 may collect further data of radar captures on multiple non-human target objects of various types and characteristics. Here, it may be advantageous to maximize the size of the data set and the variety of target objects.

At block 704, the data set may be subjected to postprocessing to extract features that can be utilized to distinguish human vs. non-human target objects. For example, one or more of the features described above in relation to equations 1-10 may be extracted from the data set, as well as any other suitable features that are useful for distinguishing the target objects.

At block 706, a classifier model may be constructed and trained based on the extracted features and the collected data set. That is, the extracted features may be utilized to train and validate the performance of a classifier based on the known categorization of the samples in the data set. And at block 708, an SVM may be established by mapping the feature space and computing the distance from mapped data points from a determined boundary (e.g., in a multi-dimensional feature space, a hyper-plane boundary). At block 710, the constructed human classifier's performance may be tested for accuracy in real-time based on detection of unknown (to the classifier) target objects, both human and non-human. When the classifier's reliability is suitably high then the classifier may be deployed to users.

Figure 8:
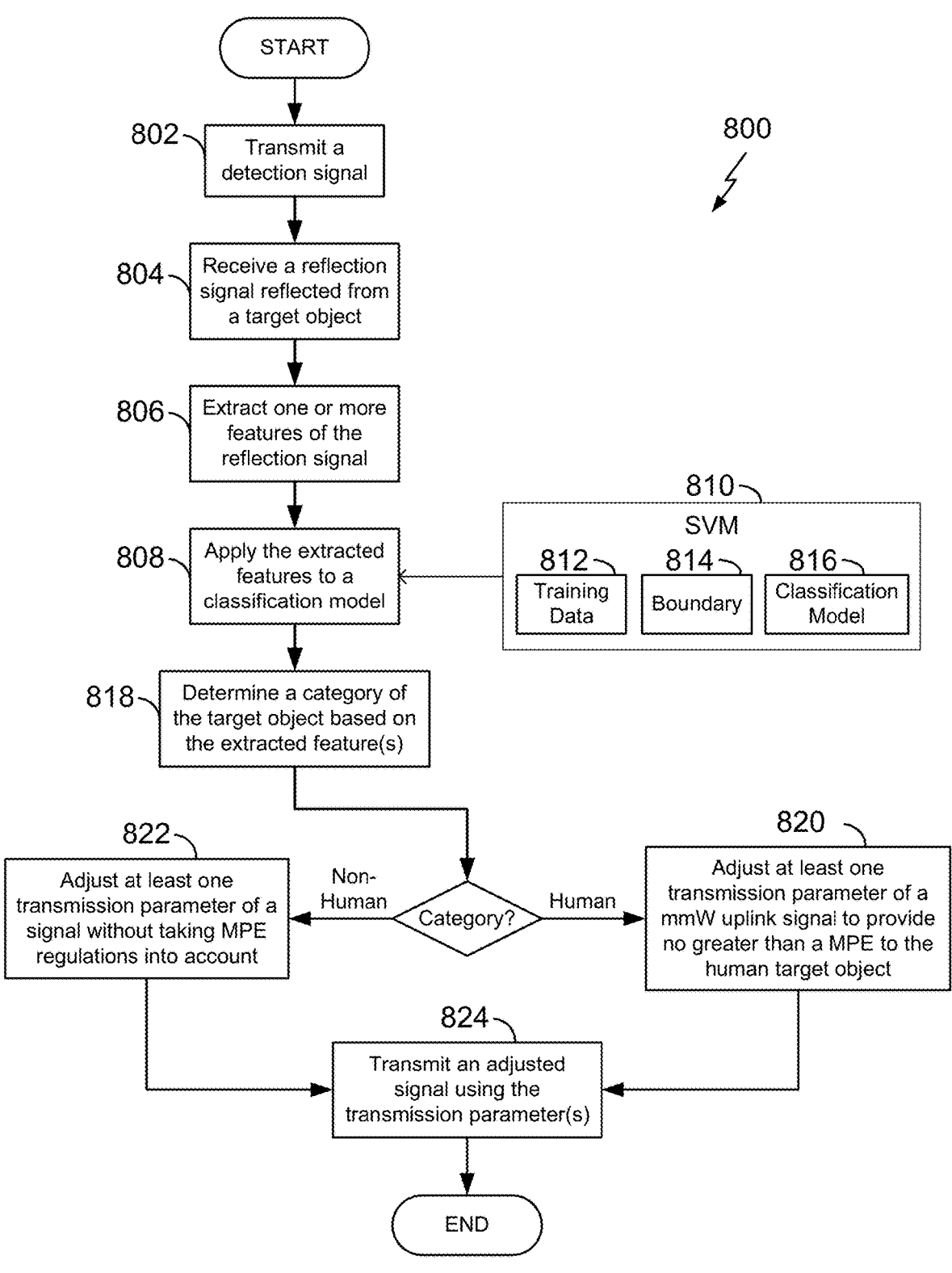
FIG. 8 is a flow chart illustrating an exemplary process for utilizing a target object classifier to control one or more transmission parameters according to some aspects of the disclosure.

FIG. 8 is a flow chart illustrating an exemplary process for classifying target objects in accordance with some aspects of the present disclosure. Though human may be used as an example, any living animal may be the basis of adjusting transmission power. As described below, some or all illustrated features may be omitted in a particular implementation within the scope of the present disclosure, and some illustrated features may not be required for implementation of all embodiments. In some examples, the process may be carried out by the electronic device 102 illustrated in FIG. 1 or 2. In some examples, the process may be carried out by the various components of the electronic device, including but not limited to a transceiver 120 and processor or DSP circuitry 122 as illustrated in FIG. 3. In some examples, the process of FIG. 8 may be carried out by any suitable apparatus or means for carrying out the functions or algorithm described below.

At block 802, an electronic device 102 may transmit a detection signal. For example, a transceiver 120 may utilize one or more antennas, such as a transmit antenna 210-1 to transmit a pulse, an FMCW signal, a multi-tone signal, or any other suitable signal for radar-based proximity detection. At block 804, the electronic device 102 may receive a reflection signal reflected from a target object. For example, the transceiver 120 may utilize one or more antennas, such as a receive antenna 210-2 to receive the reflection signal.

At block 806, the electronic device 102 may extract one or more features of the reflection signal. For example, feature extraction circuitry 326 may process information corresponding to the reflection signal, such as the spectra of one or more radar samples of the reflection signal, to determine one or more features useful for characterizing the target object. In some examples, a given feature may correspond to a single realization, or reflection from the target object. In other examples, a given feature may correspond to a plurality of realizations, such as a sequence of any suitable number of realizations.

At block 808, the electronic device 102 may apply the extracted features to a classification model. For example, an SVM 810 may be configured according to a set of training data 812 to establish one or more boundaries 814. The boundary or boundaries may be configured to separate classes of target objects in a feature space, based on features extracted from reflection signals received off target objects. The establishment of the boundary 814 based on the training data 812 may be according to a classification model 816 established utilizing the process described above and illustrated in FIG. 7.

If the category of the target object indicates that the target object is human, then at block 820, the electronic device 102 may adjust at least one transmission parameter of a transmission signal, such as a mmW uplink signal, to provide no greater than a maximum permissible exposure (MPE) of the mmW signal to the human target object. For example, the electronic device 102 may adjust at least one of a power level of the uplink signal, a beam steering angle of the uplink signal, a frequency of the uplink signal, a selected antenna of the uplink signal, a communication protocol of the uplink signal, or a combination of the above, such that the power of the uplink signal at the human target object is no greater than the MPE regulatory requirements. On the other hand, if the category of the target object indicates that the target object is non-human, then at block 822 the electronic device 102 may adjust at least one transmission parameter of a transmission signal without taking MPE regulations into account. For example, the electronic device may adjust the transmission parameter(s) in such a way that the power of the transmitted signal may exceed an MPE level at the non-human target object. At block 824, the electronic device 102 may transmit an adjusted signal using the adjusted transmission parameter, as described above.

If the category of the target object indicates that the target object is human, then at block 820, the electronic device 102 may adjust at least one transmission parameter of a transmission signal, such as a mmW uplink signal, to provide no greater than a maximum permissible exposure (MPE) of the mmW signal to the human target object. For example, the electronic device 102 may adjust at least one of a power level of the uplink signal, a beam steering angle of the uplink signal, a frequency of the uplink signal, a selected antenna of the uplink signal, a communication protocol of the uplink signal, or a combination of the above, such that the power of the uplink signal at the human target object is no greater than the MPE regulatory requirements. On the other hand, if the category of the target object indicates that the target object is non-human, then at block 822 the electronic device 102 may adjust at least one transmission parameter of a transmission signal without taking MPE regulations into account. For example, the electronic device may adjust the transmission parameter(s) in such a way that the power of the transmitted signal may exceed an MPE level at the non-human target object. At block 824, the electronic device 102 may transmit an adjust signal using the adjusted transmission parameter, as described above.

The process shown in FIG. 8 may include additional aspects, such as any single aspect or any combination of aspects described below and/or in connection with one or more other processes described elsewhere herein.

In a first aspect, an electronic device may adjust one or more transmission parameters based on a determined category of a target object. Here, the transmission parameter may be at least one of a power level, a beam steering angle, a frequency, a selected antenna, a communication protocol, or some combination of the above.

In a second aspect, alone or in combination with the first aspect, the category of the target object may be one of: a human target object, or a non-human target object; an animal target object, or a non-animal target object; or a living target object, or a non-living target object.

In a third aspect, alone or in combination with one or more of the first and second aspects, an electronic device may determine, based on one or more features of a reflection signal, a category of a target object. Here, the one or more features of the reflection signal may include one or more features indicative of micromovements characteristic of a human target object.

In a fourth aspect, alone or in combination with one or more of the first through third aspects, the determining the category of the target object may include extracting one or more features of a reflection signal, applying the one or more extracted features to a classification model configured with a boundary that separates objects, within a feature space, into categories, determining a location of the target object, within the feature space, relative to the boundary, and identifying the category of the target object based on the location within the feature space.

In a fifth aspect, alone or in combination with one or more of the first through fourth aspects, the classification model corresponds to a support vector machine (SVM). Here, the boundary within the feature space is determined based on a set of training data.

In a sixth aspect, alone or in combination with one or more of the first through fifth aspects, the adjusted signal includes a millimeter-wave (mmW) signal. Here, the category of the target object is a human target object, and the adjusting at least one transmission parameter includes configuring the adjusted signal to provide no greater than a maximum permissible exposure (MPE) of the mmW signal to the human target object.

In a seventh aspect, alone or in combination with one or more of the first through sixth aspects, the one or more features of the reflection signal include at least one of: a variance of a dynamic time warping of a series of realizations sampling the target object; a maximum of the dynamic time warping of the series of realizations sampling the target object; a variance of a difference between a peak power in each realization of the series of realizations sampling the target object, and an average peak power across the series of realizations sampling the target object; a variance of a difference between a distance where a peak power lies in each realization of the series of realizations sampling the target object, and an average distance where the peak power lies in the series of realizations sampling the target object; a spread of peak power of a discrete Fourier transform (DFT) of the series of realizations sampling the target object; a variance of the peak power of the DFT of the series of realizations sampling the target object; a variance of a change in power measured in consecutive realizations sampling the target object; a variance of a distance at which a peak power occurs in consecutive realizations sampling the target object; a variance of a real part of time domain samples of a realization sampling the target object; a variance of an imaginary part of time domain samples of the realization sampling the target object; or combinations thereof.

In an eighth aspect, alone or in combination with one or more of the first through seventh aspects, the electronic device, or a wireless communication device, includes a housing shaped and sized to carry one or more components, including a memory, a wireless transceiver, a power amplifier, and at least one processor. Here, the memory stores data configured to enable the at least one processor to process object-sensing information against stored data, thereby enabling classification of one or more objects into one or more object-type classes.

In a ninth aspect, alone or in combination with one or more of the first through eighth aspects, the wireless transceiver is configured to engage in mmW communication and mmW object sensing substantially simultaneously.

In a tenth aspect, alone or in combination with one or more of the first through ninth aspects, the wireless communication device includes an antenna module having an array of antenna elements, wherein the power amplifier is configured to dynamically provide power to selected ones of the antenna elements for moderation of the transmission parameter and/or for beamforming.

In an eleventh aspect, alone or in combination with one or more of the first through tenth aspects, the wireless communication device includes an interface circuit for interfacing with an auxiliary device spaced apart from the housing. The interface circuit is configured to enable communication between the wireless communication device and the auxiliary device such that the wireless communication device receives object-sensing information from the auxiliary device, and in response, moderates a transmission parameter associated with the wireless transceiver transmitting and/or receiving millimeter waves.

In a twelfth aspect, alone or in combination with one or more of the first through eleventh aspects, the at least one processor is configured to determine whether sensed objects can be associated with one or more object classes, wherein the one or more object classes comprise: non-human tissue, human tissue, or a combination thereof.

In a thirteenth aspect, alone or in combination with one or more of the first through twelfth aspects, the wireless transceiver is configured to sense objects ranging from about 1 to about 360 degrees such that the at least one processor can yield an object-sensing map of objects exterior to said housing.

In a fourteenth aspect, alone or in combination with one or more of the first through thirteenth aspects, the at least one processor is configured to produce a map based at least on the object-sensing information, wherein the map identifies objects relative to the wireless communication device.

In a fifteenth aspect, alone or in combination with one or more of the first through fourteenth aspects, the wireless transceiver is configured to sense objects relative to and exterior the housing via mmW signaling via repetitive transmission of millimeter wave signals toward one or more objects and repetitive receipt of mmW signals from the one or more objects such that the wireless transceiver is configured to observe micromovements occurring by the one or more objects.

In a sixteenth aspect, alone or in combination with one or more of the first through fifteenth aspects, the wireless communication device receives signaling from one or more other wireless communication devices indicating that any one of the other wireless communications has moderated one or more wireless transmission parameters based on the object-class information.

In a seventeenth aspect, alone or in combination with one or more of the first through sixteenth aspects, the wireless communication device determines surrounding information of objects located around the one or more other wireless communication devices.

In an eighteenth aspect, alone or in combination with one or more of the first through seventeenth aspects, the wireless transmission parameter relates to power of transmitted or received millimeter-wave signals.

In a nineteenth aspect, alone or in combination with one or more of the first through eighteenth aspects, the wireless communication device is configured as a vehicle. Here, the at least one processor is configured to control one or more operating parameters of the vehicle body based at least in part on the object-sensing information.

In a twentieth aspect, alone or in combination with one or more of the first through nineteenth aspects, the wireless communication device is configured for gaming. Here, one or more user interfaces are positioned proximate a housing of the gaming device, and the at least one processor is further configured to receive user input via the one or more user interfaces positioned proximate the housing and in response to convey object sensing information to a user.

In a twenty-first aspect, alone or in combination with one or more of the first through twentieth aspects, the gaming device includes a visible interface field defining a visual display configured to visually convey object sensing information to the user.

In a twenty-second aspect, a wireless communication device transmits a plurality of detection signals; receives, corresponding to the plurality of detection signals, a plurality of reflection signals reflected from a proximate object; and transmits a transmission signal having a transmission parameter based on variations over time in one or more features of the plurality of reflection signals.

In a twenty-third aspect, alone or in combination with the twenty-second aspect, the transmission parameter comprises at least one of a power level, a beam steering angle, a frequency, a selected antenna, or a communication protocol.

In a twenty-fourth aspect, alone or in combination with one or more of the twenty-second through twenty-third aspects, the variations over time in the one or more features of the plurality of reflection signals comprise one or more features indicative of micromovements characteristic of a human.

In a twenty-fifth aspect, alone or in combination with one or more of the twenty-second through twenty-fourth aspects, the wireless communication device further extracts the one or more features of the plurality of reflection signals; applies the one or more extracted features to a classification model configured with a boundary that separates objects, within a feature space, into categories; determining a location of the proximate object, within the feature space, relative to the boundary; identifies a category of the proximate object based on the location within the feature space; and adjusts the transmission parameter based on the category of the proximate object.

In a twenty-sixth aspect, alone or in combination with one or more of the twenty-second through twenty-fifth aspects, the transmission signal comprises a millimeter-wave signal, and the transmission parameter comprises a transmission power level having no greater than a maximum permissible exposure of the millimeter-wave signal to the proximate object when the variations over time in the one or more features of the plurality of reflection signals indicate that the proximate object is a human.

In a twenty-seventh aspect, alone or in combination with one or more of the twenty-second through twenty-sixth aspects, the variations over time in the one or more features of the plurality of reflection signals comprise at least one of: a variance of a dynamic time warping of the plurality of reflection signals; a maximum of the dynamic time warping of the plurality of reflection signals; a variance of a difference between a peak power in each reflection signal of the plurality of reflection signals, and an average peak power across the plurality of reflection signals; a variance of a difference between a distance where a peak power lies in each reflection signal of the plurality of reflection signals, and an average distance where the peak power lies in the plurality of reflection signals; a spread of peak power of a discrete Fourier transform (DFT) of the plurality of reflection signals; a variance of the peak power of the DFT of the plurality of reflection signals; a variance of a change in power measured in consecutive reflection signals of the plurality of reflection signals; a variance of a distance at which a peak power occurs in consecutive reflection signals of the plurality of reflection signals; a variance of a real part of time domain samples of the plurality of reflection signals; or a variance of an imaginary part of time domain samples of the plurality of reflection signals.

In one configuration, an electronic device 102 includes means for transmitting a detection signal, means for receiving a reflection signal reflected from a target object, and means for transmitting an adjusted signal using a transmission parameter. In one aspect, the aforementioned means may be the transceiver 120. In one aspect, the aforementioned means may be the processor(s) or DSP circuitry 128 shown in FIGS. 1 and 3, configured to perform the functions recited by the aforementioned means. In another aspect, the aforementioned means may be a circuit or any apparatus configured to perform the functions recited by the aforementioned means. The electronic device 102 may further include means for determining, based on one or more features of a reflection signal, a category of the target object, and means for adjusting at least one transmission parameter based on the category of the target object. In one aspect, the aforementioned means may be the processor(s) or DSP circuitry 128 shown in FIGS. 1 and 3, configured to perform the functions recited by the aforementioned means. In another aspect, the aforementioned means may be a circuit or any apparatus configured to perform the functions recited by the aforementioned means.

Of course, in the above examples, the circuitry included in the processor or DSP circuitry 128 is merely provided as an example, and other means for carrying out the described functions may be included within various aspects of the present disclosure, including but not limited to the instructions stored in the computer-readable storage medium 110, or any other suitable apparatus or means described in any one of the FIGS. 1, 2, and/or 3, and utilizing, for example, the processes and/or algorithms described herein in relation to FIG. 8.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-8 may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-8 may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A method of wireless communication comprising:
transmitting a plurality of detection signals;
receiving, corresponding to the plurality of detection signals, a plurality of reflection signals reflected from an object;
categorizing, based on variations over time of measurements of the plurality of reflection signals, the object as a living object or a non-living object, wherein the variations over time of the measurements comprise at least one of:
a variance of a dynamic time warping of the plurality of reflection signals;
a maximum of the dynamic time warping of the plurality of reflection signals;
a variance of a difference between a peak power in each reflection signal of the plurality of reflection signals, and an average peak power across the plurality of reflection signals;
a variance of a difference between a distance where a peak power lies in each reflection signal of the plurality of reflection signals, and an average distance where the peak power lies in the plurality of reflection signals;
a variance of a real part of time domain samples of the plurality of reflection signals; or
a variance of an imaginary part of time domain samples of the plurality of reflection signals; and
transmitting, using a transmission parameter, a transmission signal, wherein:
the transmission parameter is a first transmission parameter if the object is categorized as the living object; and
the transmission parameter is a second transmission parameter if the object is categorized as the non-living object, wherein the second transmission parameter is different from the first transmission parameter.

2. The method of claim 1, wherein the transmission parameter comprises at least one of a power level, a beam steering angle, a frequency, a selected antenna, or a communication protocol.

3. The method of claim 1, wherein the plurality of reflection signals are indicative of micromovements characteristic of a living object, and wherein categorizing the object comprises categorizing the object as the living object.

4. The method of claim 1, wherein categorizing the object based on the variations over time of the measurements of the plurality of reflection signals comprises:
extracting one or more features of the plurality of reflection signals;
applying the one or more extracted features to a classification model configured with a boundary that separates objects within a feature space;
determining a location of the object, within the feature space, relative to the boundary; and
categorizing the object as the living object or the non-living object based on the location within the feature space.

5. The method of claim 1,
wherein the first transmission parameter comprises a first transmission power level constrained according to a maximum permissible exposure (MPE) requirement; and wherein the second transmission parameter comprises a second transmission power level that is not constrained according to the MPE requirement.

6. The method of claim 5, wherein the transmission signal comprises a millimeter-wave signal.

7. The method of claim 1, wherein the variations over time of the measurements of the plurality of reflection signals are the variance of the dynamic time warping of the plurality of reflection signals.

8. The method of claim 1, wherein the variations over time of the measurements of the plurality of reflection signals are the maximum of the dynamic time warping of the plurality of reflection signals.

9. The method of claim 1, wherein the variations over time of the measurements of the plurality of reflection signals are the variance of the difference between the peak power in each reflection signal of the plurality of reflection signals, and the average peak power across the plurality of reflection signals.

10. The method of claim 1, wherein the variations over time of the measurements of the plurality of reflection signals are the variance of the difference between the distance where the peak power lies in each reflection signal of the plurality of reflection signals, and the average distance where the peak power lies in the plurality of reflection signals.

11. The method of claim 1, wherein the variations over time of the measurements of the plurality of reflection signals are the variance of the real part of time domain samples of the plurality of reflection signals.

12. The method of claim 1, wherein the variations over time of the measurements of the plurality of reflection signals are the variance of the imaginary part of time domain samples of the plurality of reflection signals.

13. A wireless communication device comprising:
one or more processors; and
a transceiver coupled to the one or more processors, wherein the one or more processors are coupled to a memory, and wherein the wireless communication device is configured to:
transmit a plurality of detection signals;
receive corresponding to the plurality of detection signals, a plurality of reflection signals reflected from an object;
categorize, based on variations over time of measurements of the plurality of reflection signals, the object as a living object or a non-living object, wherein the variations over time of the measurements comprise at least one of:

a variance of a dynamic time warping of the plurality of reflection signals;

a maximum of the dynamic time warping of the plurality of reflection signals;

a variance of a difference between a peak power in each reflection signal of the plurality of reflection signals, and an average peak power across the plurality of reflection signals;

a variance of a difference between a distance where a peak power lies in each reflection signal of the plurality of reflection signals, and an average distance where the peak power lies in the plurality of reflection signals;

a variance of a real part of time domain samples of the plurality of reflection signals; or a variance of an imaginary part of time domain samples of the plurality of reflection signals; and transmit, using a transmission parameter, a transmission signal, wherein:

the transmission parameter is a first transmission parameter if the object is categorized as the living object; and the transmission parameter is a second transmission parameter if the object is categorized as the non-living object, wherein the second transmission parameter is different from the first transmission parameter.

14. The wireless communication device of claim 13, wherein the transmission parameter comprises at least one of a power level, a beam steering angle, a frequency, a selected antenna, or a communication protocol.

15. The wireless communication device of claim 13, wherein the plurality of reflection signals are indicative of micromovements characteristic of a living object, and wherein, to categorize the object, the wireless communication device is configured to categorize the object as the living object.

16. The wireless communication device of claim 13, wherein the wireless communication device configured to:

extract one or more features of the plurality of reflection signals;

apply the one or more extracted features to a classification model configured with a boundary that separates objects within a feature space;

determine a location of the object, within the feature space, relative to the boundary; and categorize the object as the living object or the non-living object based on the location within the feature space.

17. The wireless communication device of claim 13, wherein the first transmission parameter comprises a first transmission power level constrained according to a maximum permissible exposure (MPE) requirement; and wherein the second transmission parameter comprises a second transmission power level that is not constrained according to the MPE requirement.

18. The wireless communication device of claim 17, wherein the transmission signal comprises a millimeter-wave signal.

19. An apparatus for wireless communication comprising:

means for transmitting a plurality of detection signals;

means for receiving, corresponding to the plurality of detection signals, a plurality of reflection signals reflected from an object;

means for categorizing, based on variations over time of measurements of the plurality of reflection signals, the object as a living object or a non-living object, wherein the variations over time of the measurements comprise at least one of:

a variance of a dynamic time warping of the plurality of reflection signals;

a maximum of the dynamic time warping of the plurality of reflection signals;

a variance of a difference between a peak power in each reflection signal of the plurality of reflection signals, and an average peak power across the plurality of reflection signals;

a variance of a difference between a distance where a peak power lies in each reflection signal of the plurality of reflection signals, and an average distance where the peak power lies in the plurality of reflection signals;

a variance of a real part of time domain samples of the plurality of reflection signals; or a variance of an imaginary part of time domain samples of the plurality of reflection signals; and means for transmitting, using a transmission parameter, a transmission signal, wherein:

the transmission parameter is a first transmission parameter if the object is categorized as the living object; and the transmission parameter is a second transmission parameter if the object is categorized as the non-living object, wherein the second transmission parameter is different from the first transmission parameter.

20. The apparatus of claim 19, wherein the transmission parameter comprises at least one of a power level, a beam steering angle, a frequency, a selected antenna, or a communication protocol.

21. The apparatus of claim 19, wherein the plurality of reflection signals are indicative of micromovements characteristic of a living object, and wherein the means for categorizing the object comprises means for categorizing the object as the living object.

22. The apparatus of claim 19, wherein the means for categorizing the object based on the variations over time of the measurements of the plurality of reflection signals comprises:

means for extracting one or more features of the plurality of reflection signals;

means for applying the one or more extracted features to a classification model configured with a boundary that separates objects within a feature space;

means for determining a location of the object, within the feature space, relative to the boundary; and means for categorizing the object as the living object or the non-living object based on the location within the feature space.

23. The apparatus of claim 19, wherein the first transmission parameter comprises a first transmission power level constrained according to a maximum permissible exposure (MPE) requirement; and wherein the second transmission parameter comprises a second transmission power level that is not constrained according to the MPE requirement.

24. The apparatus of claim 23, wherein the transmission signal comprises a millimeter-wave signal.

25. A non-transitory computer readable medium having code stored thereon that, when executed, causes a wireless communication device to:

transmit a plurality of detection signals;

receive, corresponding to the plurality of detection signals, a plurality of reflection signals reflected from an object;

categorize, based on variations over time of measurements of the plurality of reflection signals, the object as a living object or a non-living object, wherein the variations over time of the measurements comprise at least one of:

a variance of a dynamic time warping of the plurality of reflection signals;

a maximum of the dynamic time warping of the plurality of reflection signals;

a variance of a difference between a peak power in each reflection signal of the plurality of reflection signals, and an average peak power across the plurality of reflection signals;

a variance of a difference between a distance where a peak power lies in each reflection signal of the plurality of reflection signals, and an average distance where the peak power lies in the plurality of reflection signals;

a variance of a real part of time domain samples of the plurality of reflection signals; or a variance of an imaginary part of time domain samples of the plurality of reflection signals; and transmit, using a transmission parameter, a transmission signal, wherein:

the transmission parameter is a first transmission parameter if the object is categorized as the living object; and the transmission parameter is a second transmission parameter if the object is categorized as the non-living object, wherein the second transmission parameter is different from the first transmission parameter.

26. The non-transitory computer readable medium of claim 25, wherein the transmission parameter comprises at least one of a power level, a beam steering angle, a frequency, a selected antenna, or a communication protocol.

27. The non-transitory computer readable medium of claim 25, wherein the plurality of reflection signals are indicative of micromovements characteristic of a living object, and wherein, to categorize the object, the code when executed causes the wireless communication device to categorize the object as the living object.

28. The non-transitory computer readable medium of claim 25, wherein, to categorize the object based on the variations over time of the measurements of the plurality of reflection signals, the code when executed causes the wireless communication device to:

extract one or more features of the plurality of reflection signals;

apply the one or more extracted features to a classification model configured with a boundary that separates objects within a feature space;

determine a location of the object, within the feature space, relative to the boundary; and categorize the object as the living object or the non-living object based on the location within the feature space.

29. The non-transitory computer readable medium of claim 25, wherein the first transmission parameter comprises a first transmission power level constrained according to a maximum permissible exposure (MPE) requirement; and wherein the second transmission parameter comprises a second transmission power level that is not constrained according to the MPE requirement.

30. The non-transitory computer readable medium of claim 29, wherein the transmission signal comprises a millimeter-wave signal.

* * * * *